United States Patent
Refai

(10) Patent No.: US 11,083,594 B2
(45) Date of Patent: Aug. 10, 2021

(54) SPINAL CAGE DEVICE, SYSTEM, AND METHODS OF ASSEMBLY AND USE

(71) Applicant: REFAI TECHNOLOGIES, LLC, Atlanta, GA (US)

(72) Inventor: Daniel Refai, Atlanta, GA (US)

(73) Assignee: REFAI TECHNOLOGIES, LLC, Atlanta, GA (US)

(*) Notice: Subject to any disclaimer, the term of this patent is extended or adjusted under 35 U.S.C. 154(b) by 160 days.

(21) Appl. No.: 16/281,842

(22) Filed: Feb. 21, 2019

(65) Prior Publication Data

US 2019/0175356 A1 Jun. 13, 2019

Related U.S. Application Data

(63) Continuation of application No. 15/121,088, filed as application No. PCT/US2015/017080 on Feb. 23, 2015, now Pat. No. 10,213,318.

(Continued)

(51) Int. Cl.

| | | |
|---|---|---|
| *A61F 2/44* | (2006.01) | |
| *A61B 17/70* | (2006.01) | |
| *A61F 2/30* | (2006.01) | |

(52) U.S. Cl.
CPC .......... *A61F 2/447* (2013.01); *A61B 17/7059* (2013.01); *A61F 2002/30331* (2013.01); *A61F 2002/30393* (2013.01); *A61F 2002/30395* (2013.01); *A61F 2002/30428* (2013.01); *A61F 2002/30431* (2013.01);

(Continued)

(58) Field of Classification Search
CPC ...................................................... A61F 2/447
See application file for complete search history.

(56) References Cited

U.S. PATENT DOCUMENTS

| | | |
|---|---|---|
| 6,159,245 A | 12/2000 | Meriwether et al. |
| 6,428,542 B1 | 8/2002 | Michelson |

(Continued)

FOREIGN PATENT DOCUMENTS

| | | |
|---|---|---|
| FR | 2822674 A1 | 10/2002 |
| WO | 20120121726 A1 | 9/2012 |

OTHER PUBLICATIONS

Extended European Search Report issued in European Patent Application No. 15755595.4 dated Oct. 30, 2017.

(Continued)

*Primary Examiner* — Andrew Yang
(74) *Attorney, Agent, or Firm* — Heslin Rothenburg Farley & Mesiti PC; Jacquelyn A. Graff, Esq.

(57) ABSTRACT

Spinal cage devices, systems, and methods of assembly and implanting the devices and systems are disclosed. The cage system includes a cage and at least one locking screw assembly configured to couple to the cage. The spinal cage system includes a cage with a body portion, an external plate, and a rod. The body portion includes at least one opening positioned between the first and second ends, a center opening in the first end, and at least one hole adjacent the center opening. The external plate includes an opening and at least two holes on opposite sides of the opening. The rod extends through the center opening in the cage, the first end configured to couple to the external plate, and the second end positioned in the at least one opening. Methods for assembling a spinal cage system and for implanting a cage system are also disclosed.

17 Claims, 26 Drawing Sheets

Related U.S. Application Data

(60) Provisional application No. 61/944,282, filed on Feb. 25, 2014.

(52) U.S. Cl.
CPC ............ *A61F 2002/30484* (2013.01); *A61F 2002/30507* (2013.01); *A61F 2002/30514* (2013.01); *A61F 2002/30553* (2013.01); *A61F 2002/30578* (2013.01); *A61F 2002/30579* (2013.01); *A61F 2002/30593* (2013.01); *A61F 2002/30785* (2013.01); *A61F 2002/30828* (2013.01); *A61F 2310/00011* (2013.01); *A61F 2310/00023* (2013.01); *A61F 2310/00071* (2013.01); *A61F 2310/00179* (2013.01)

(56) References Cited

U.S. PATENT DOCUMENTS

| | | |
|---|---|---|
| 6,436,100 B1 | 8/2002 | Berger |
| 6,569,165 B2 | 5/2003 | Wahl et al. |
| 7,077,864 B2 | 7/2006 | Byrd, III et al. |
| 7,172,627 B2 | 2/2007 | Fiere et al. |
| 8,100,972 B1 | 1/2012 | Bruffey et al. |
| 8,268,000 B2 | 9/2012 | Waugh et al. |
| 9,132,021 B2 * | 9/2015 | Mermuys ............... A61F 2/442 |
| 2006/0085071 A1 | 4/2006 | Lechmann et al. |
| 2013/0345814 A1 | 12/2013 | Walkenhorst et al. |
| 2014/0046447 A1 | 2/2014 | Dunworth et al. |
| 2014/0052255 A1 | 2/2014 | Defalco et al. |
| 2014/0100663 A1 | 4/2014 | Messerli et al. |

OTHER PUBLICATIONS

International Search Report and Written Opinion issued in PCT/US2015/017080 dated Jul. 8, 2015.

* cited by examiner

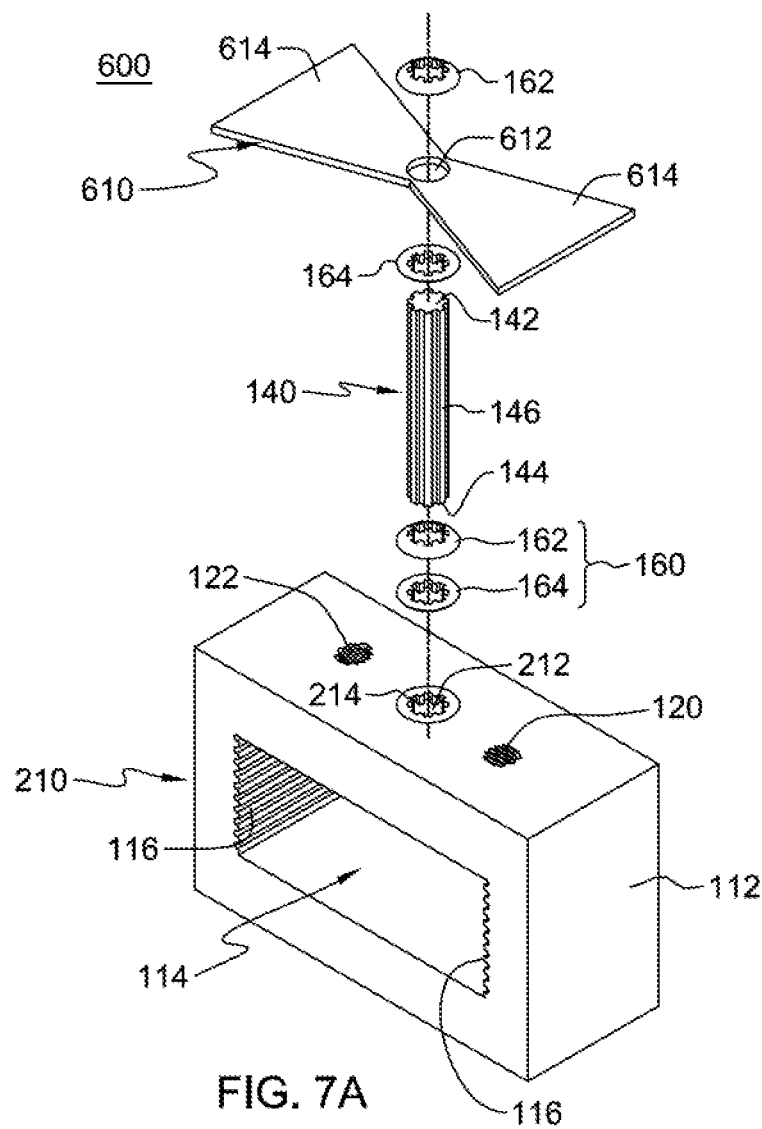
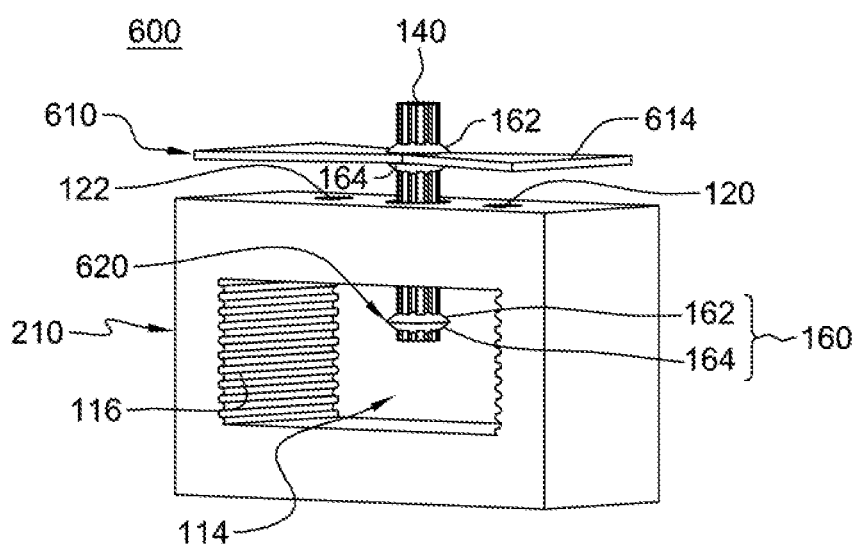
FIG. 7A
FIG. 7B

SPINAL CAGE DEVICE, SYSTEM, AND METHODS OF ASSEMBLY AND USE

CROSS-REFERENCE TO RELATED APPLICATIONS

This application is a continuation of U.S. application Ser. No. 15/121,088 filed on Aug. 24, 2016; which is a national stage filing under Section 371 of International Application No. PCT/US2015/017080 filed on Feb. 23, 2015 and published as WO 2015/130604 on Sep. 3, 2015; which also claims priority benefit to U.S. Provisional Application No. 61/944,282 filed Feb. 25, 2014, which are incorporated herein by reference in their entireties.

TECHNICAL FIELD

The present disclosure relates generally to orthopedic and neurosurgical implants and systems for insertion between two vertebral bodies in a patient's spine. More specifically, the present disclosure relates to spinal cage devices, systems, and methods of assembly and use.

BACKGROUND

Spinal cages are designed to be inserted between two vertebrae in a patient's spine to restore or maintain the spacing between two vertebrae. The cages may be designed to attach to the vertebrae in various configurations which generally involve the use of bone screws. Currently available spinal cages may experience bone screw back out which may cause destabilization of the spinal cage between the two vertebrae if fusion has not yet occurred. Additionally, as screws back out of the spinal cages they may interact with surround tissue and cause further complications for the patient.

Thus, the currently available spinal cages may cause additional complications to a patient and new spinal cages are needed to prevent additional damage from occurring to the patient.

SUMMARY

Aspects of the present invention provide spinal cage devices, systems, and methods of assembly and use that can be used to facilitate proper alignment of a patient's spine.

In one aspect, provided herein is a cage system including a cage and at least one locking screw assembly configured to couple to the cage.

In another aspect, provided herein is a spinal cage system, including a cage, an external plate, and a rod. The cage may include a body portion with a first end and a second end. The body portion may also include at least one opening positioned between the first end and the second end, a center opening in the first end and positioned relatively perpendicular to the at least one opening, and at least one hole positioned adjacent to the center opening. The external plate may include an opening and at least two holes positioned on opposite sides of the opening. The rod may also have a first end and a second end and may extend through the center opening in the cage. The first end of the rod is configured to couple to the external plate and the second end is positioned in the at least one opening.

In yet another aspect, provided herein is a method of assembling a spinal cage system including obtaining a cage, an external plate, a rod, and at least one locking mechanism. The method may also include inserting the rod into the cage. In addition, the method may include attaching a first locking mechanism of the at least one locking mechanism to a portion of the rod in the cage. Further, the method may include attaching the external plate to a portion of the rod outside of the cage.

In a further aspect, provided herein is a method of implanting a cage system in a patient's spine, including placing an incision over the spine and preparing the spine for receiving the cage system. The method may also include obtaining a cage system with a cage, at least one fastener, and at least one locking member. The method may further include inserting the cage into the spine and aligning the cage relative to two adjacent vertebral bodies. In addition, the method may include evaluating the position of the cage and inserting at least one fastener through the cage into one of the two adjacent vertebral bodies. The method may also include positioning the at least one locking member in the cage adjacent to the fastener. Further, the method may include activating the at least one locking member to secure the at least one fastener in the cage. Finally, the method may include closing the incision.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description and claims herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 7A is an exploded view of an embodiment of a spinal cage system, in accordance with an aspect of the present invention;

FIG. 7B is an isometric view of the assembled spinal cage system of FIG. 7A, in accordance with an aspect of the present invention;

DETAILED DESCRIPTION OF EMBODIMENTS

Figure 1A:
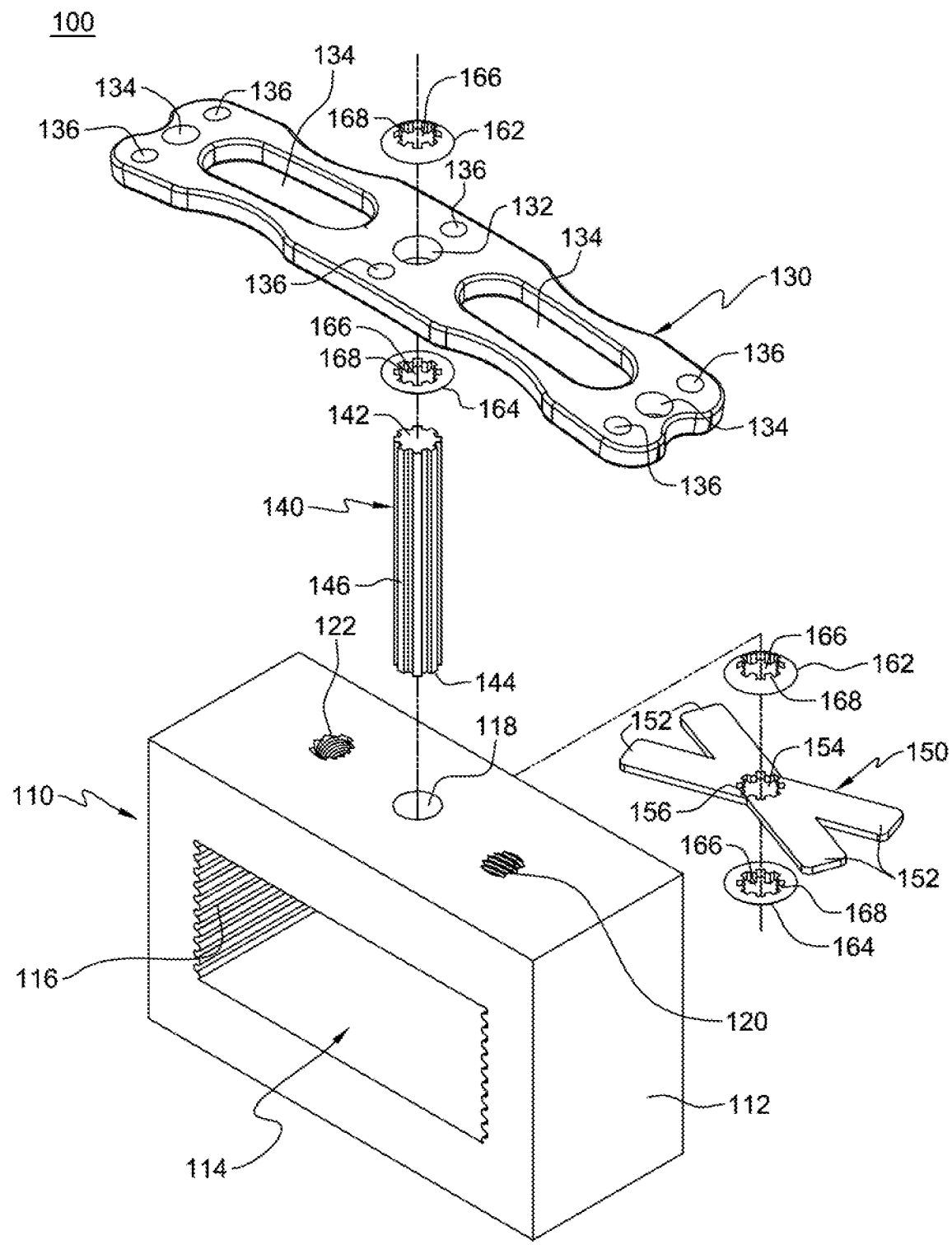
FIG. 1A is an exploded view of an embodiment of a spinal cage system, in accordance with an aspect of the present invention.

Generally stated, disclosed herein are embodiments of spinal cage devices and systems. Further, methods of assembling and using the spinal cage devices and systems are discussed.

In this application, the words proximal, distal, anterior, posterior, medial and lateral are defined by their standard usage for indicating a particular part or portion of a bone or prosthesis coupled thereto, or directional terms of reference, according to the relative disposition of the natural bone. For example, "proximal" means the portion of a bone or prosthesis nearest the torso, while "distal" indicates the portion of the bone or prosthesis farthest from the torso. As an example of directional usage of the terms, "anterior" refers to a direction towards the front side of the body, "posterior" refers to a direction towards the back side of the body, "medial" refers to a direction towards the midline of the body and "lateral" refers to a direction towards the sides or away from the midline of the body.

Referring to the drawings, wherein like reference numerals are used to indicate like or analogous components throughout the several views, and with particular reference to FIGS. 1A-1E, there is illustrated an embodiment of a spinal cage system 100. The spinal cage system 100 may include a cage 110, an external plate 130, a rod 140, and an internal plate 150.

Figure 1B:
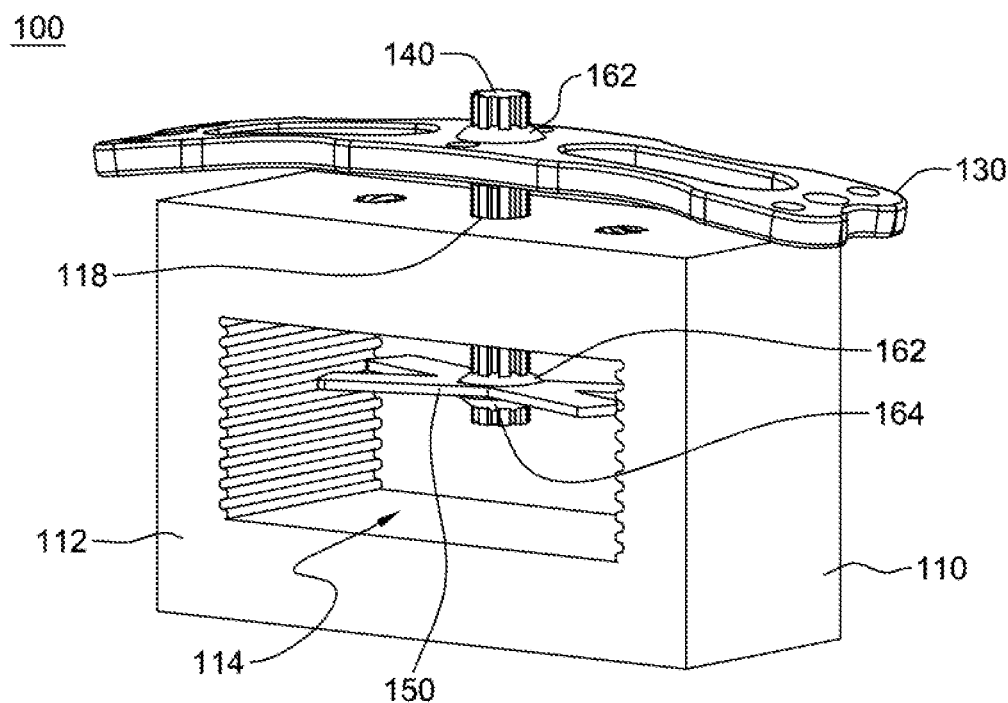
FIG. 1B is an isometric view of the assembled spinal cage system of FIG. 1A, in accordance with an aspect of the present invention.
Figure 1C:
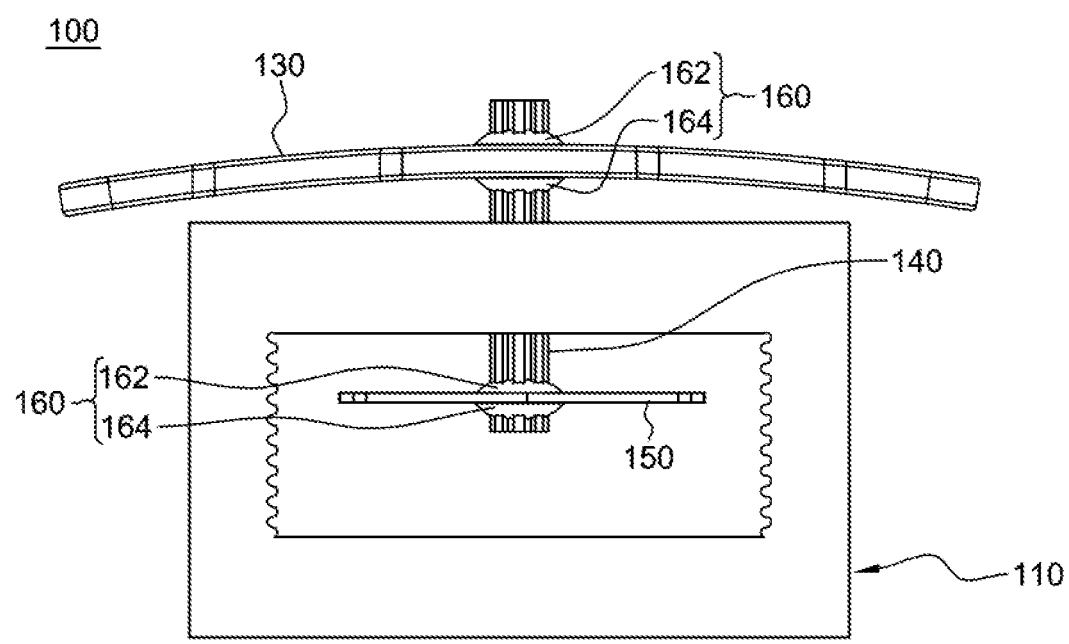
FIG. 1C is a top view of the spinal cage system of FIG. 1B, in accordance with an aspect of the present invention.

As shown in FIGS. 1A-1E, the cage 110 may include a body portion 112 with at least one opening 114 through the cage to, for example, allow for bone fusion between two adjacent vertebral bodies in the spine. The at least one opening 114, as shown in FIGS. 1A-1C, extends from a superior surface to an inferior surface of the cage 110. It is also contemplated that additional openings 114 may also extend, for example, from a first side to a second side, from an anterior surface to a superior surface, and/or between any combination of the surfaces of the cage 110 to enable insertion and placement of bone graft material. The at least one opening 114 may also include, for example, a plurality of protrusions 116 along one or more interior surface of the cage 110. The plurality of protrusions 116 may be used, for example, to assist with bone fusion or the positioning of the external plate 130 by being able to receive the internal plate 150. The plurality of protrusions 116 may also be, for example, a coating or alternatively shaped interior surface structure to assist with bone fusion.

Figure 1D:
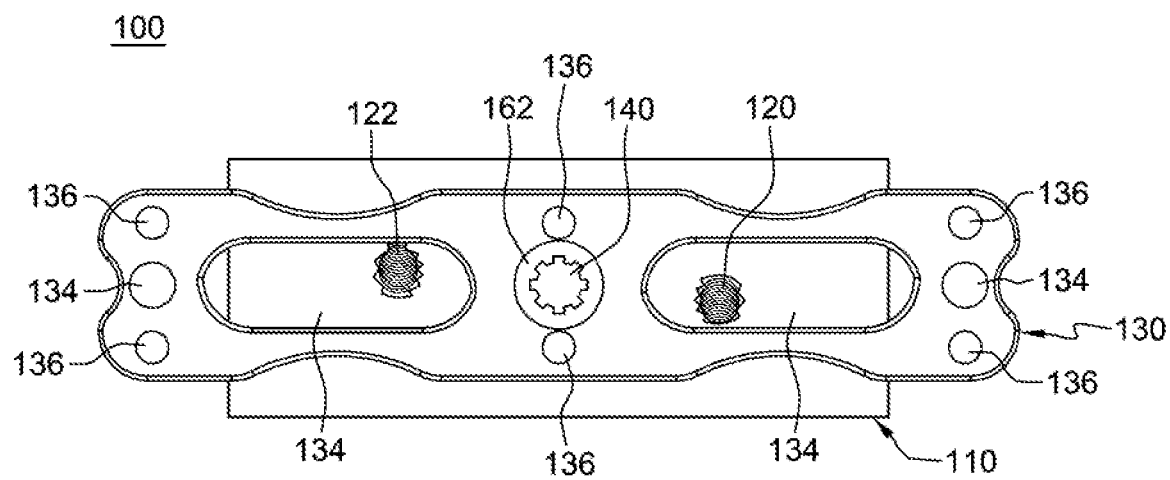
FIG. 1D is an anterior view of the spinal cage system of FIG. 1B, in accordance with an aspect of the present invention.
Figure 1E:
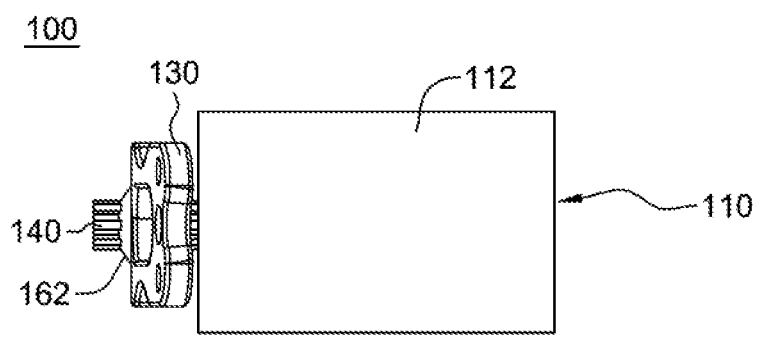
FIG. 1E is a side view of the spinal cage system of FIG. 1B, in accordance with an aspect of the present invention.
Figure 9A:
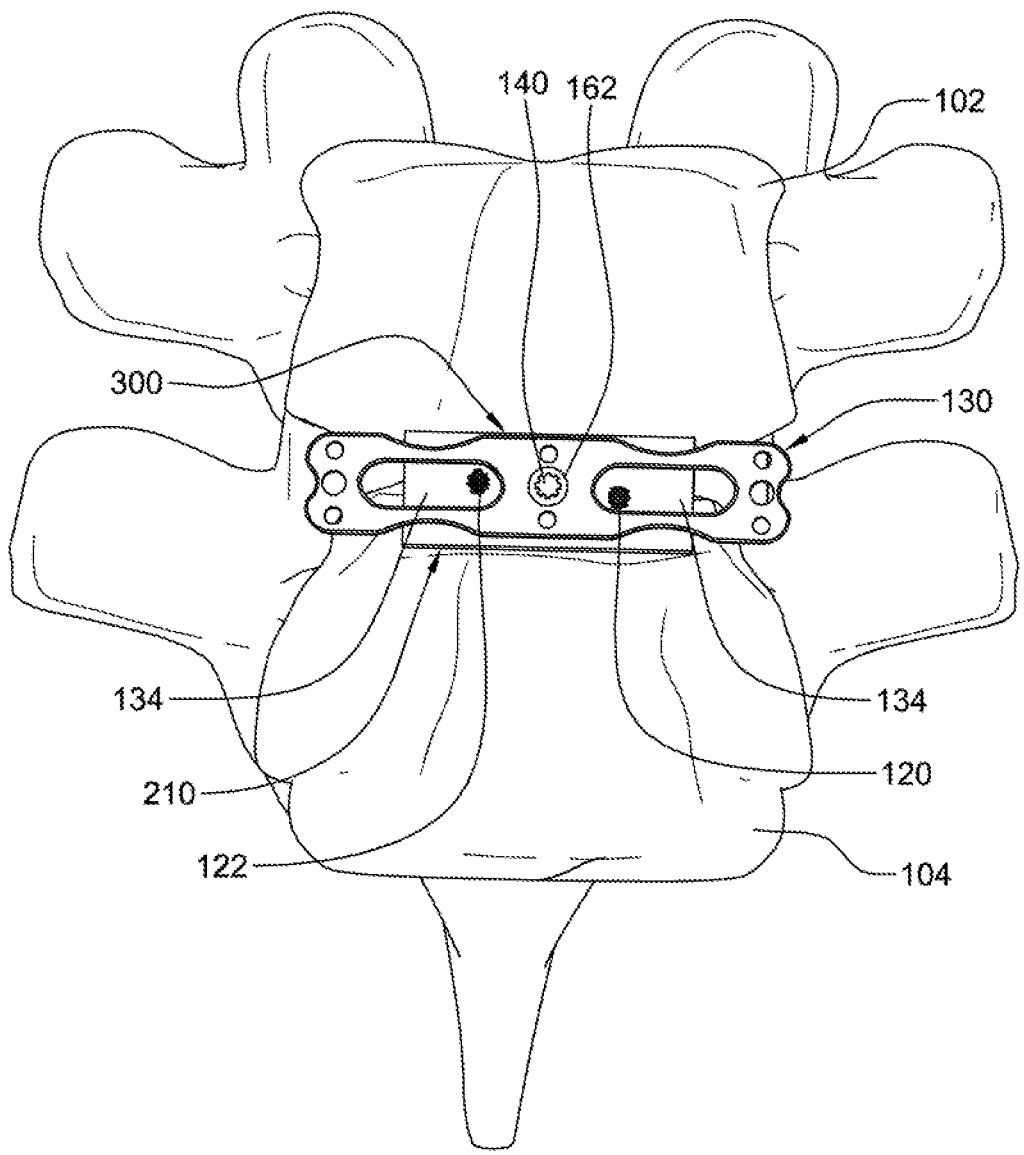
FIG. 9A is an anterior view of a portion of a patient's spine with the spinal cage system of FIG. 1B inserted between two vertebral bodies in the spine, in accordance with an aspect of the present invention.
Figure 9B:
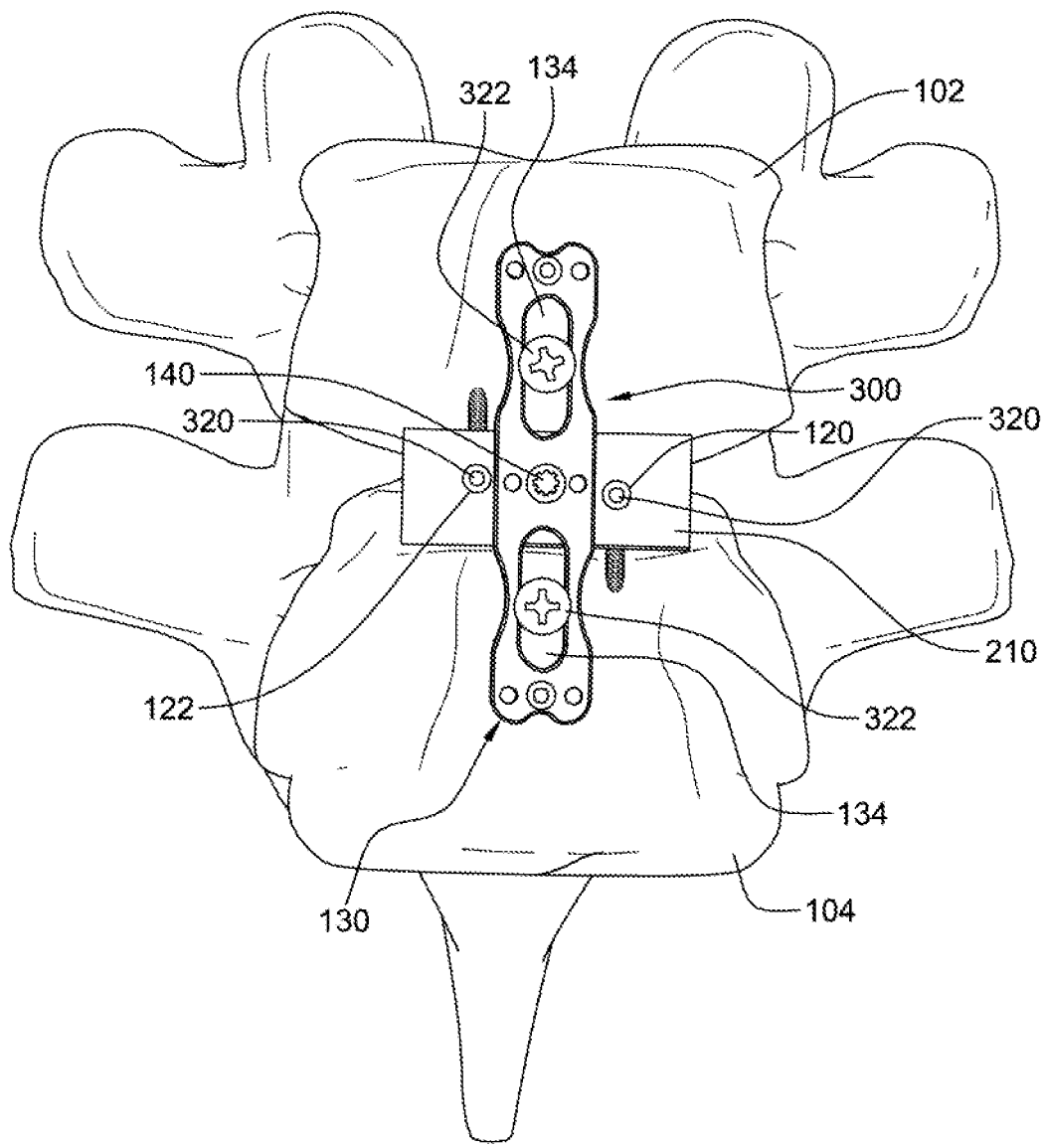
FIG. 9B is an anterior view of FIG. 9A with the spinal cage system secured to the patient's vertebral bodies, in accordance with an aspect of the present invention.

As shown in FIGS. 1A, 1B, and 1D, the cage 110 may also include an opening 118, a first hole 120, and a second hole 122 on the anterior surface of the cage 110. The opening 118 may be sized to receive the rod 140. The terms "opening," "center opening" and "rod opening" may be used interchangeably herein as they refer to the same opening 118. The first hole 120 and the second hole 122 may be, for example, holes for receiving fasteners, such as bone screws (not shown). The first hole 120 and the second hole 122 may be angled with respect to a top surface of the cage 110 to enable insertion of the fasteners into the vertebral bodies adjacent to the cage 110. In the depicted embodiment, the first hole 120 is angled to allow for insertion of a fastener into a proximal vertebral body and the second hole 122 is angled to allow for insertion of a fastener into a distal vertebral body, as shown in FIG. 9B. Alternative configurations of the first hole 120 and the second hole 122 are also contemplated, including, but not limited to, the first hole 120 being angled toward the distal vertebral body and the second hole 122 being angled toward the proximal vertebral body, as well as, both holes 120, 122 being angled in the same direction.

The external plate 130 may include an opening 132, at least two holes 134, and a plurality of additional holes 136 each extending from a top surface to a bottom surface of the external plate 130. The opening 132 may be sized to receive the rod 140. The at least two holes 134 may be, for example, holes for securing the external plate 130 to a patient's vertebral bodies using, for example, fasteners, such as bone screws. The at least two holes 134 may be positioned, for example, with one to the right of the opening 132 and a second to the left of the opening 132. In the depicted embodiments of FIGS. 1A, 1B, and 1D, the at least two holes 134 are elongated holes providing the surgeon multiple positions for insertion of a fastener into the patient's vertebral bodies to secure the external plate 130 to the vertebral bodies. For example, as depicted in FIGS. 1A and 1D, the external plate 130 includes four holes 134, two of the holes 134 are elongated holes and two are sized to correspond to the size of the fastener and are positioned on the outer ends of the external plate 130. The holes 134 may be, for example, straight, angled, or shaped to allow for insertion of a bone fastener at an angle. The external plate 130 may be secured to the patient's vertebral bodies, for example, to prevent the cage 110 from backing out of the patient's vertebral bodies.

It is also contemplated that the spinal cage system 100 may be used with an alternative external plate 170, as shown in FIGS. 3A-3D. The external plate 170 may be similar to external plate 130 except the at least two holes 134 will be sized to correspond to the size of the fasteners. Changing the at least two holes 134 from elongated holes to approximately the size of a fastener provides for only one position for insertion of the fastener through the external plate 130 into the patient's vertebral bodies. It is also contemplated that the spinal cage system 100 may be used with other alternative external plates.

Both external plates 130, 170 may also include the plurality of additional holes 136 which may be sized to receive, for example, fixations pins to hold the external plate 130, 170 in the desired position while it is secured to the patient's bones. Alternatively, the plurality of additional holes 136 may be holes to provide the surgeon with additional visualization to assist in positioning the external plate 130, 170 on the patient's spine. Further, the external plates 130, 170 may have a length sized based on the surgical procedure being performed and the length may be, for example, approximately the same length as the cage 110, longer than the cage 110, or smaller than the cage 110. External plates 130, 170 which are longer than the cage 110 may be used, for example, to span multiple levels of a patient's spine.

With continued reference to FIGS. 1A-1E, the rod 140 may include a first end 142 and a second end 144. The rod 140 may also include a plurality of grooves 146 extending from the first end 142 to the second end 144. Alternative embodiments of the rod 140 are also contemplated including, but not limited to, a smooth rod, a threaded rod, a screw, an alternative grooved embodiment, or a combination of any of these. For example, the rod 140 may include at least one grooved portion or threaded portion and at least one smooth portion. The rod 140 may be sized to be received in opening 118 of the cage 110 and to allow for the rod to slide in an anterior/posterior direction within the cage 110 both prior to and after insertion into a patient. The rod 140 may also be sized to either allow for rotation of the rod 140 within the opening 118 of the cage 110 or to fix the rod 140 from rotating within the opening 118 of the cage 110. In an alternative embodiment, the opening 118 may be threaded to receive a threaded rod. In addition, the rod 140 may be sized to be received in the opening 132 in the external plate 130 and the at least one opening 154 in the internal plate 150. The rod 140 may be made of, for example, a metal material, such as titanium, nickel, or the like, or alternatively a metal alloy, such as nitinol or the like.

The internal plate 150, as shown in FIGS. 1A-1E, may include a plurality of extension members 152 and at least one opening 154. As shown in FIGS. 1A-1B, the internal plate 150 may include, for example, four extension members 152 and the opening 154 may be positioned, for example, centered between the four extension members 152. The opening 154 may also include a plurality of protrusions or teeth 156 extending into the opening 154. The plurality of protrusions 156 may be designed to correspond to the plurality of grooves 146 of the rod 140. The internal plate 150 is designed to allow for bone fasteners to pass through the cage 110 and into a patient's surrounding vertebral bodies without engaging the internal plate 150. In addition, the internal plate 150 may be configured to enable at least one extension member 152 to act as a cutting blade to cut into at least one adjacent vertebral body endplate. If the extension members 152 are made to engage the surrounding vertebral bodies, then the internal plate 150 may be used for temporary placement of the spinal cage system 100 while fasteners are inserted into the cage 110 and/or the external plate 130.

The spinal cage system 100 may also include at least one locking mechanism 160, as shown in FIG. 1C. The locking mechanism 160 may include, for example, a top member 162 and a bottom member 164, as illustrated in FIGS. 1A-1E. The top member 162 and the bottom member 164 may each include an opening 166 and a plurality of protrusions or teeth 168 surrounding the opening. The plurality of protrusions 168 may be positioned to engage the plurality of grooves 146 in the rod 140. In one embodiment, the top member 162 may be configured to couple directly to the bottom member 164. Alternatively, the top member 162 and bottom member 164 may be configured to secure a plate, for example, the external plate 130, the internal plate 150, or the like, to the rod 140, as shown in FIGS. 1B-1C. By securing the external plate 130 and/or internal plate 150 to the rod 140 this enables a surgeon to rotate either the external plate 130 or the rod 140 to rotate the internal plate 150. The locking mechanisms 160 may be, but are not limited to, for example, washers, grub screws, threaded washers, and the like. In addition, the locking mechanisms 160 may be made of, for example, a metal material, such as, titanium, nickel, or the like.

As shown in FIGS. 1B-1C, the spinal cage system 100 may be assembled using, for example, at least one locking mechanism 160. In one embodiment, the spinal cage system 100 may be assembled by inserting the rod 140 into the opening 118 in the cage 110. Once the rod 140 is inserted into the cage 110, the internal plate 150 may be secured to the rod 140 using at least one locking mechanism 160 by, for example, first sliding the top member 162 of the locking mechanism 160 onto the rod 140, then sliding the internal plate 150 onto the rod 140, and finally sliding the bottom member 164 of the locking mechanism 160 onto the rod 140. Next the top member 162 and bottom member 164 of the locking mechanism 160 may be secured together to hold the internal plate 150 to the rod 140. The top member 162 may be secured to the bottom member 164 by, for example, press fitting the top member 162 and the bottom member 164 together. Other locking mechanisms are also contemplated for securing a plate 130, 150 to a rod 140 both in fixed position and to enable rotation of the plate 130, 150 relative to the rod 140.

The external plate 130 may also be secured to the rod 140 using at least one locking mechanism 160, as shown in FIG. 1C. The external plate 130 may be secured by, for example, sliding a bottom member 164 of the locking mechanism 160 onto the rod 140, then the external plate 130 may be slid over the rod 140, and finally the top member 162 of the locking mechanism 160 may be slid over the rod 140. Next the top member 162 and bottom member 164 may be secured together to attach the external plate 130 to the rod 140. In one embodiment, after securing the external plate 130 to the rod 140, the external plate 130 may rotate relative to the rod 140 and in another embodiment rotation of the external plate 130 will cause rotation of the rod 140 and vice versa. If the external plate 130 is secured to the rod 140, such that they rotate together, then the internal plate 150 may also rotate relative to the external plate 130 when the internal plate 150 is fixed to the rod 140. Thereby, allowing the internal plate 150 to be positioned such that the bone fasteners may be inserted through the cage 110 without interfering with the internal plate 150.

In addition to rotation of the external plate 130, the external plate 130 may also translate relative to the anterior surface of the cage 110. The translation of the external plate 130 allows for the plate to be secured to the patient's vertebral bodies either flush with the cage 110 or not flush with the cage 110. Thus, the size of the rod 140 determines the amount of translation that the external plate 130 may move relative to the cage 110. Alternative locking mechanisms 160 to secure the internal and external plates 150, 130, respectively, to the rod 140 are also contemplated. It is also contemplated that the rod 140 may be secured to the external plate 130 prior to insertion into the cage 110 and securing of the internal plate 150 to the rod.

Figure 2A:
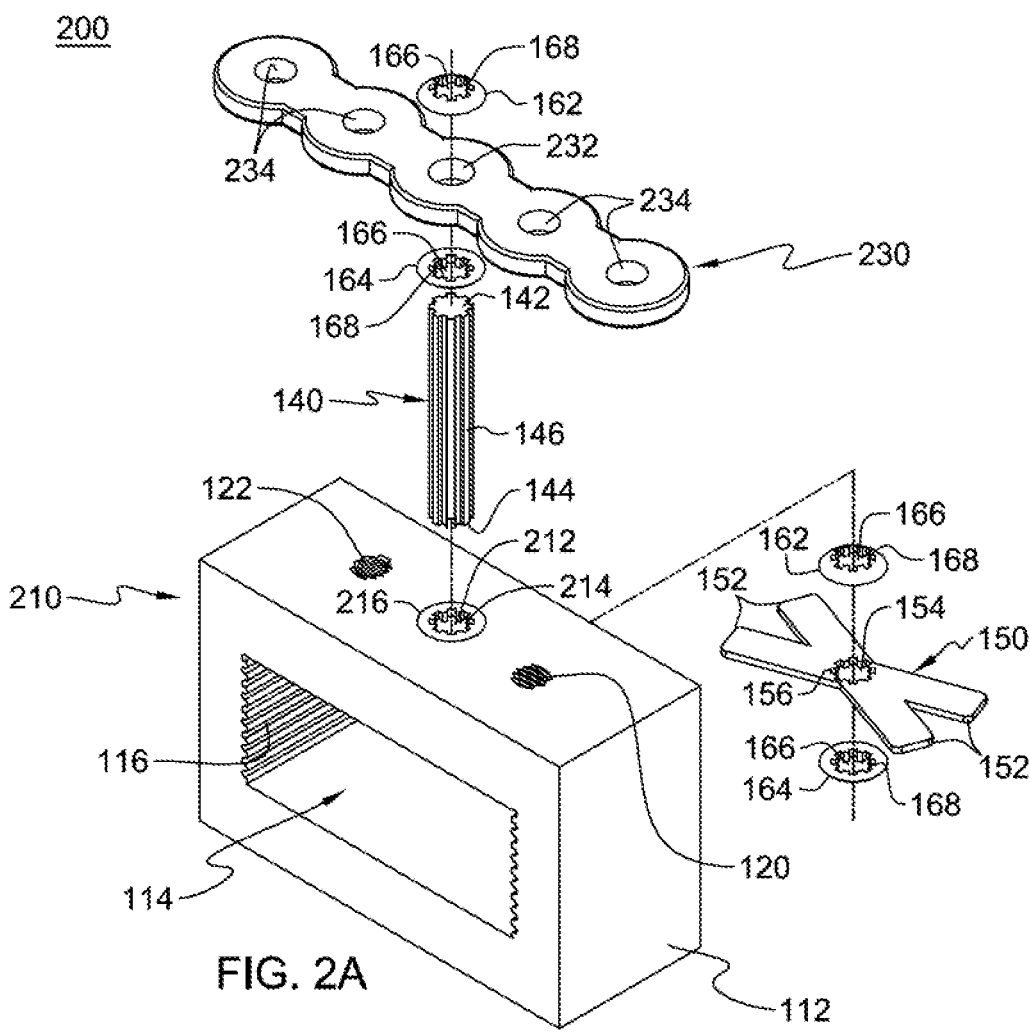
FIG. 2A is an exploded view of an embodiment of a spinal cage system, in accordance with an aspect of the present invention.
Figure 2B:
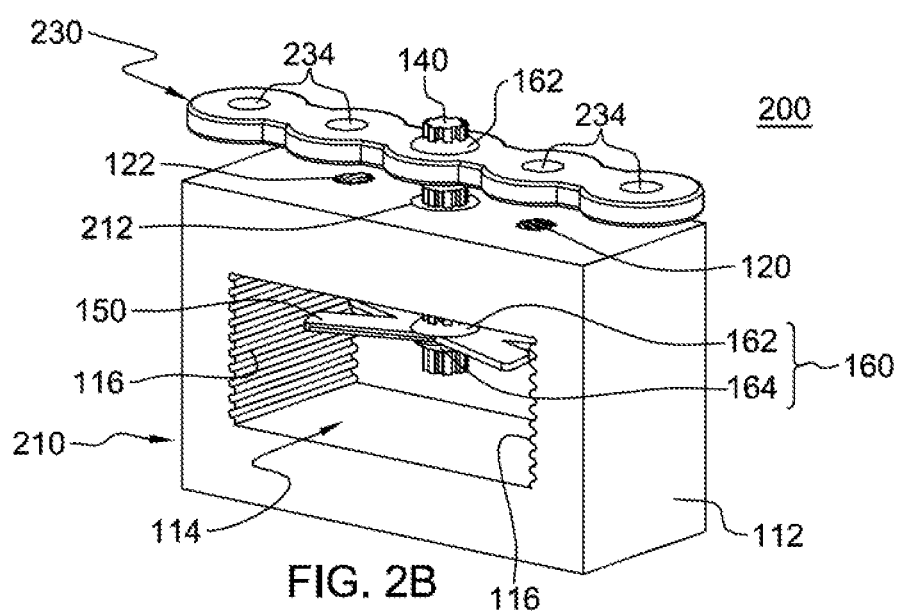
FIG. 2B is an isometric view of the assembled spinal cage system of FIG. 2A, in accordance with an aspect of the present invention.
Figure 2C:
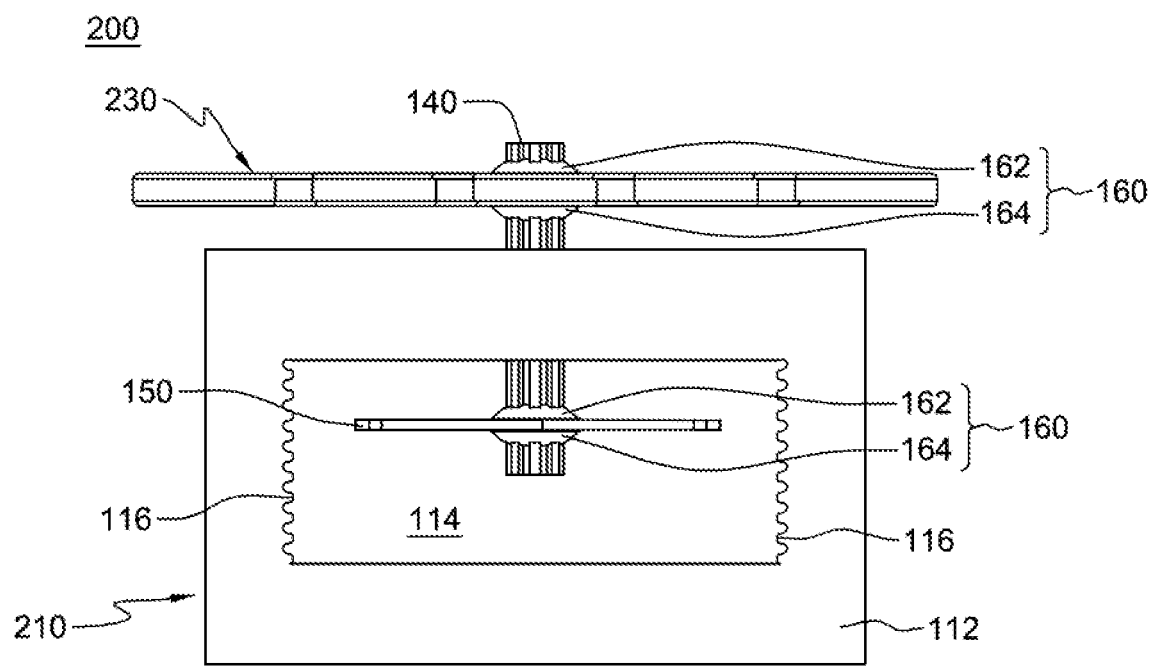
FIG. 2C is a top view of the spinal cage system of FIG. 2B, in accordance with an aspect of the present invention.
Figure 2D:
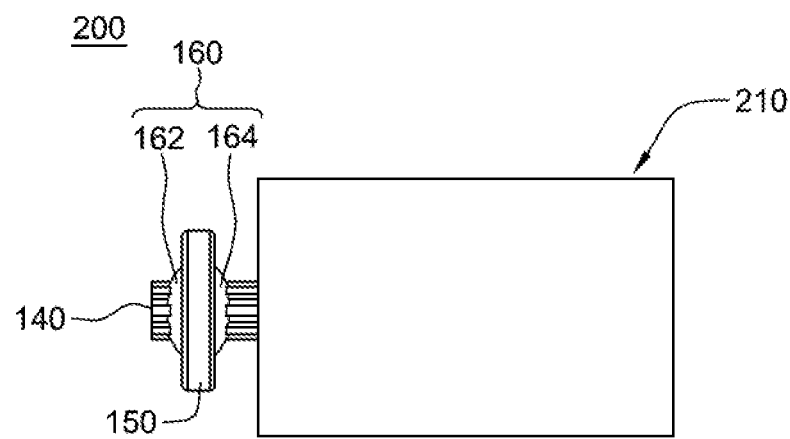
FIG. 2D is a side view of the spinal cage system of FIG. 2B, in accordance with an aspect of the present invention.
Figure 2E:
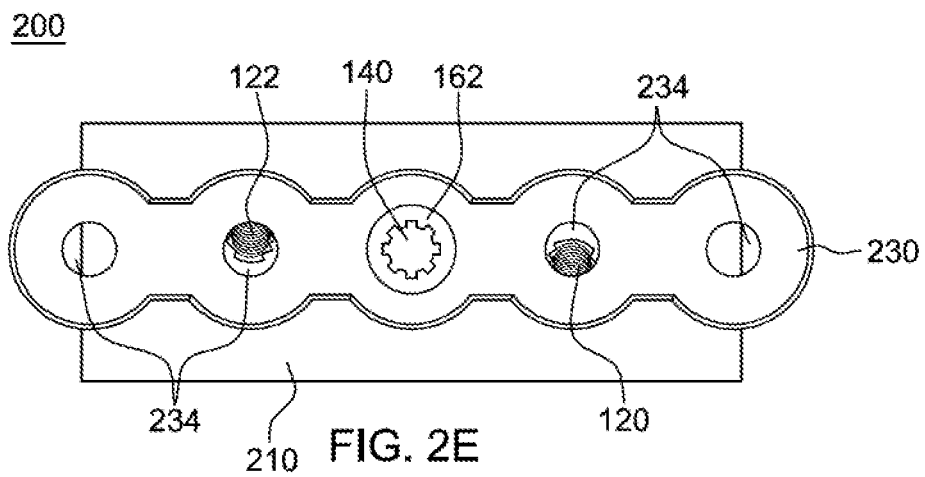
FIG. 2E is an anterior view of the spinal cage system of FIG. 2B, in accordance with an aspect of the present invention.
Figure 2F:
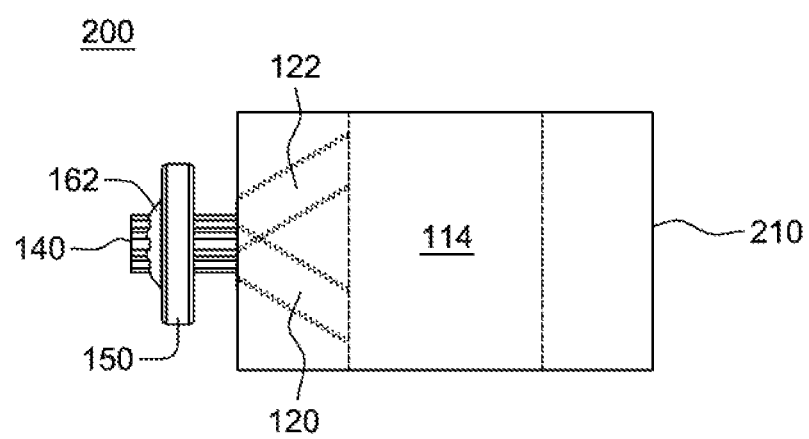
FIG. 2F is a semi-transparent side view of the spinal cage system of FIG. 2B showing the central opening and angled screw holes, in accordance with an aspect of the present invention.
Figure 3A:
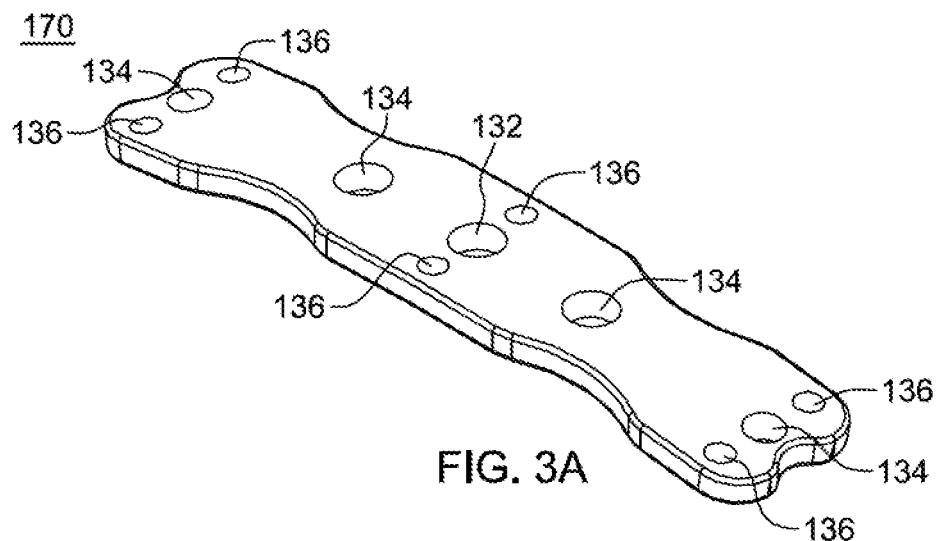
FIG. 3A is an isometric view of an alternative embodiment of a plate for the spinal cage systems of FIGS. 1 and 2, in accordance with an aspect of the present invention.
Figure 3B:
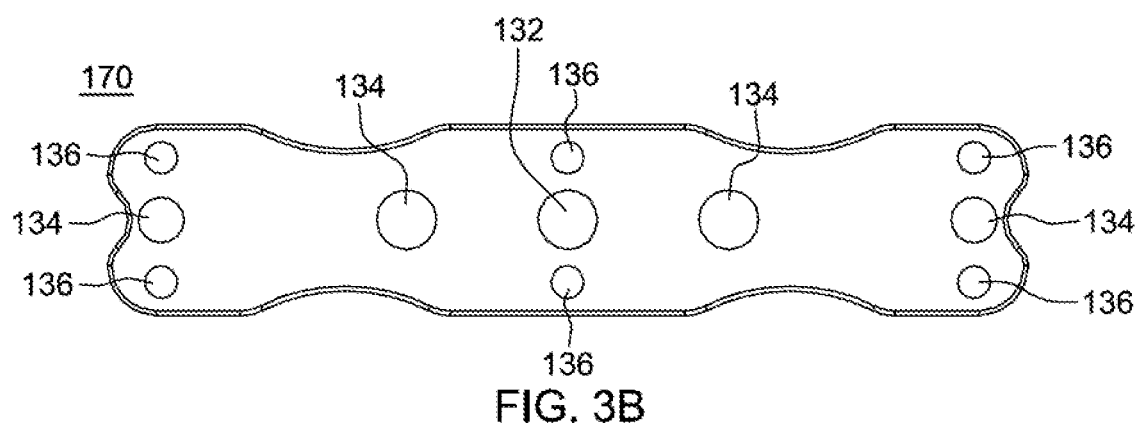
FIG. 3B is a top view of the plate of FIG. 3A, in accordance with an aspect of the present invention.
Figure 3C:
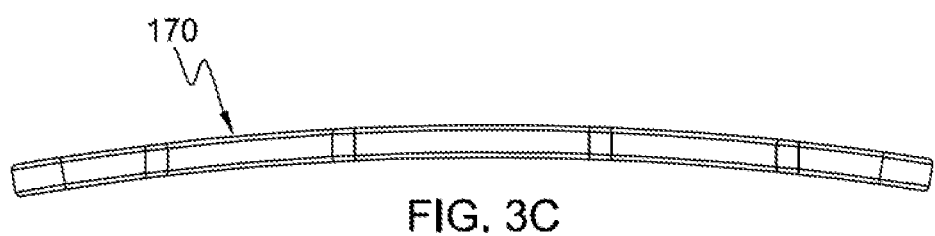
FIG. 3C is a side view of the plate of FIG. 3A, in accordance with an aspect of the present invention.
Figure 3D:
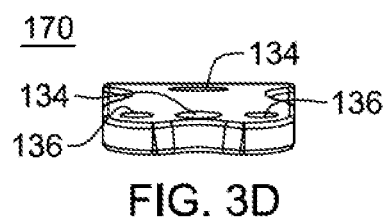
FIG. 3D is a side view of the plate of FIG. 3A, in accordance with an aspect of the present invention.
Figure 4A:
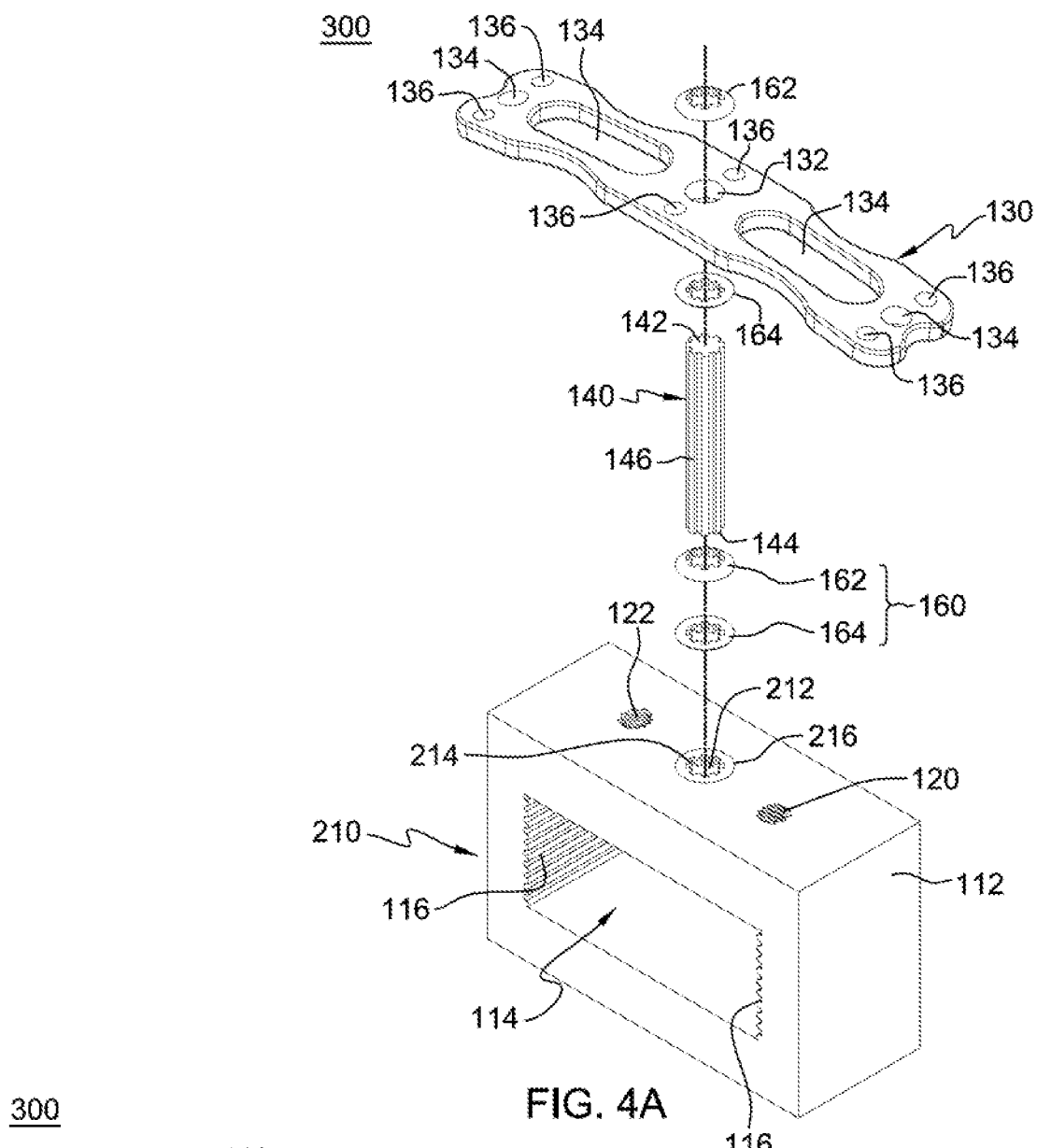
FIG. 4A is an exploded view of an embodiment of a spinal cage system, in accordance with an aspect of the present invention.
Figure 4B:
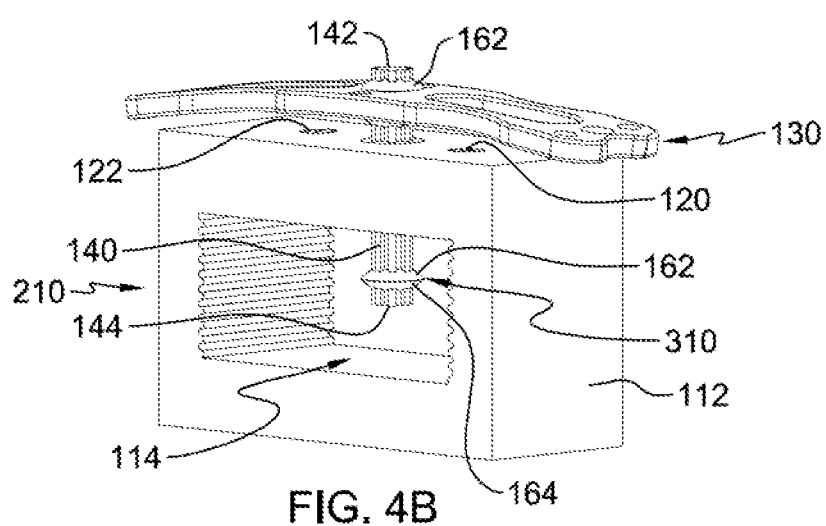
FIG. 4B is an isometric view of the assembled spinal cage system of FIG. 4A, in accordance with an aspect of the present invention.
Figure 4C:
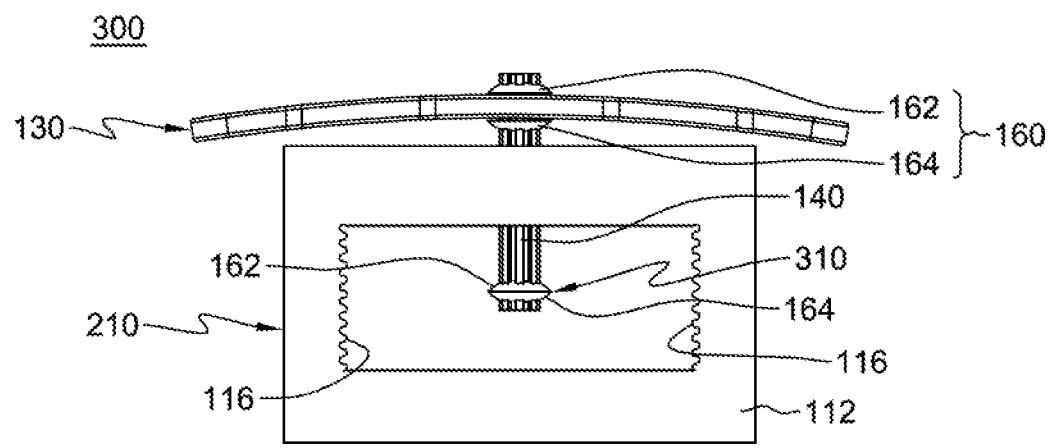
FIG. 4C is a top view of the spinal cage system of FIG. 4B, in accordance with an aspect of the present invention.
Figure 4D:
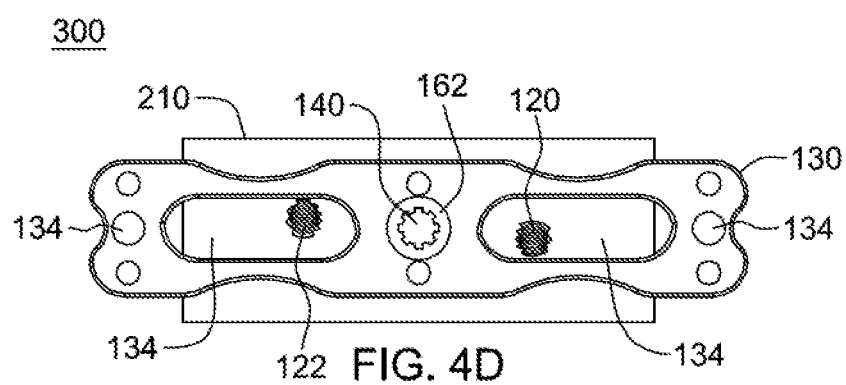
FIG. 4D is an anterior view of the spinal cage system of FIG. 4B, in accordance with an aspect of the present invention.
Figure 4E:
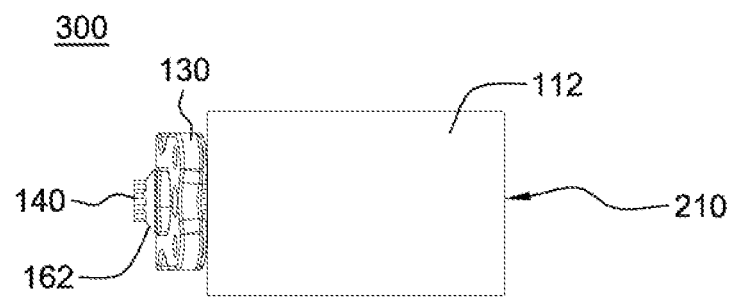
FIG. 4E is a side view of the spinal cage system of FIG. 4B, in accordance with an aspect of the present invention.
Figure 5A:
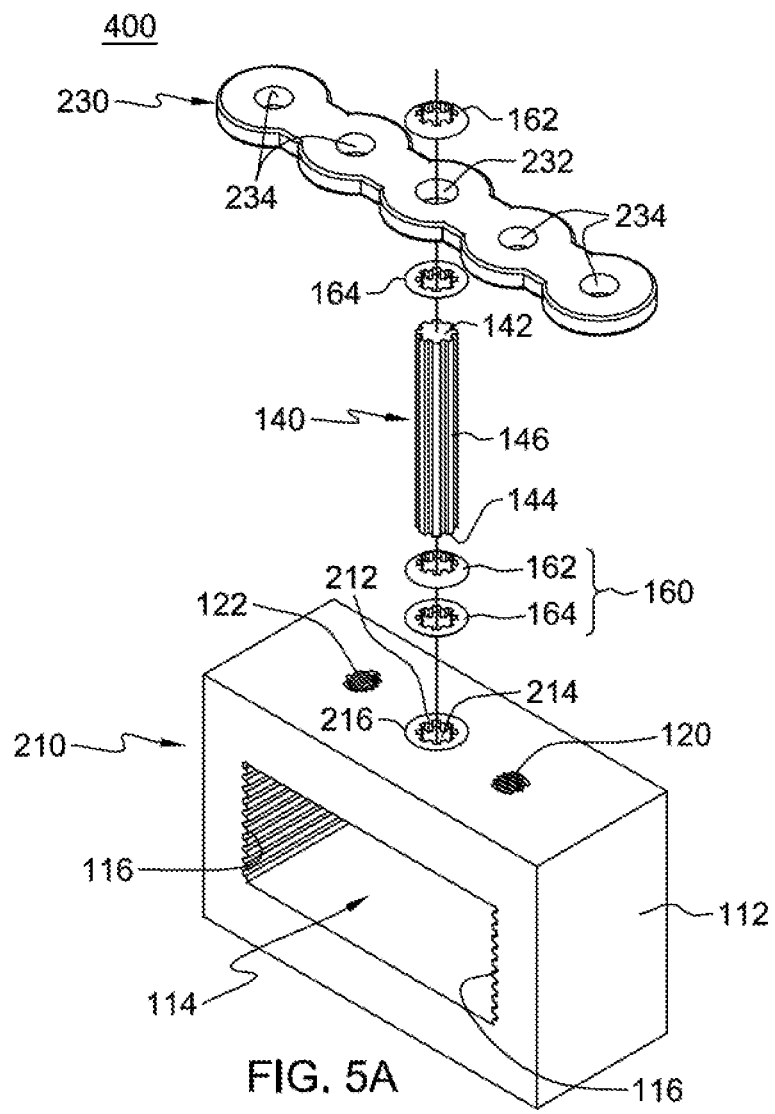
FIG. 5A is an exploded view of an embodiment of a spinal cage system, in accordance with an aspect of the present invention.
Figure 5B:
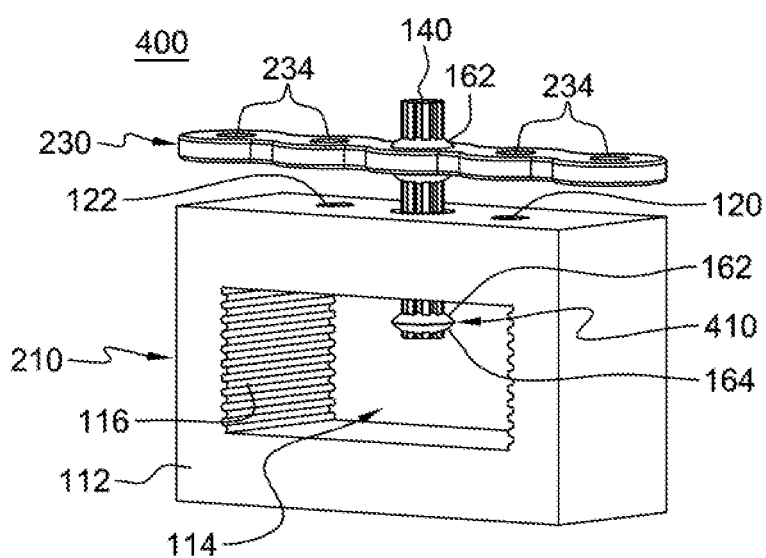
FIG. 5B is an isometric view of the assembled spinal cage system of FIG. 5A, in accordance with an aspect of the present invention.
Figure 5C:
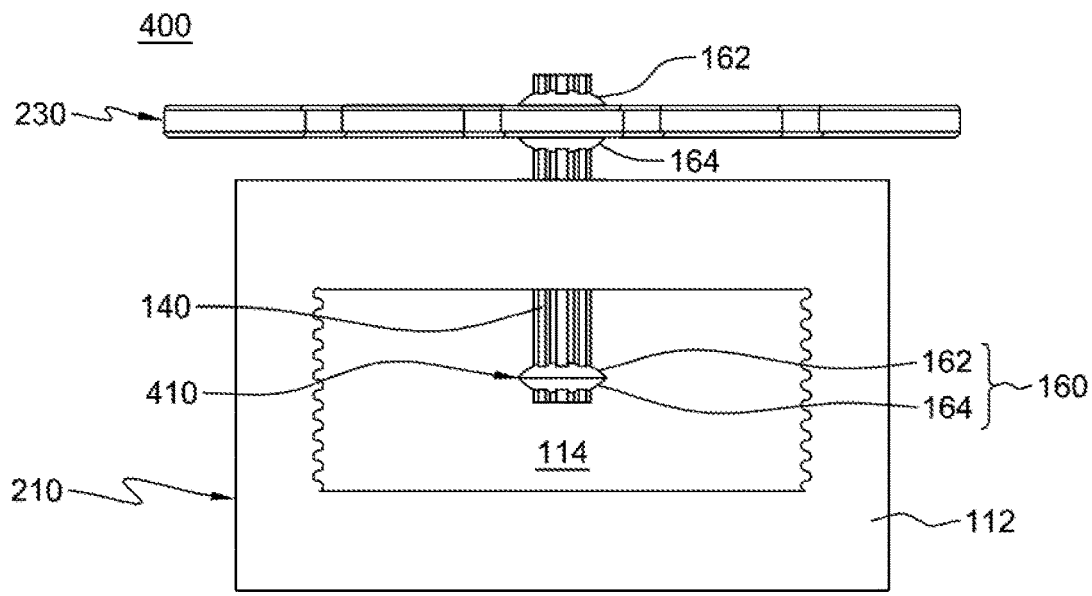
FIG. 5C is a top view of the spinal cage system of FIG. 5B, in accordance with an aspect of the present invention.
Figure 5D:
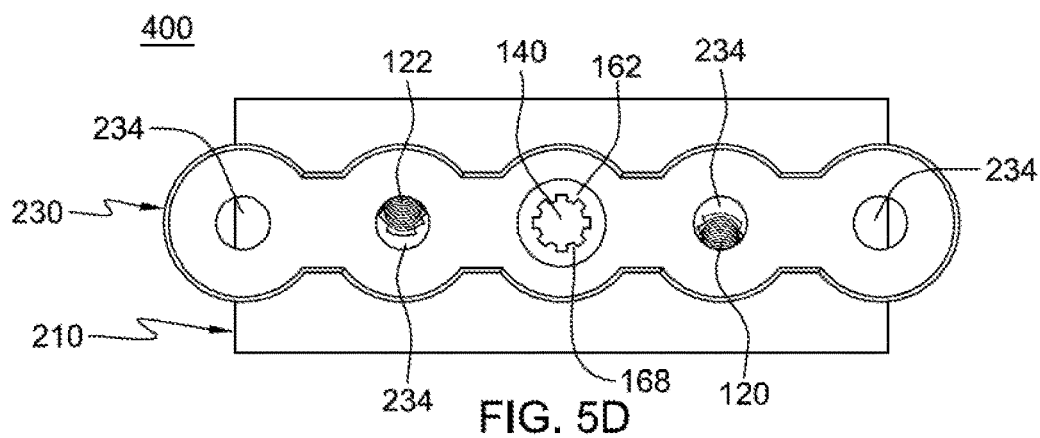
FIG. 5D is an anterior view of the spinal cage system of FIG. 5B, in accordance with an aspect of the present invention.
Figure 5E:
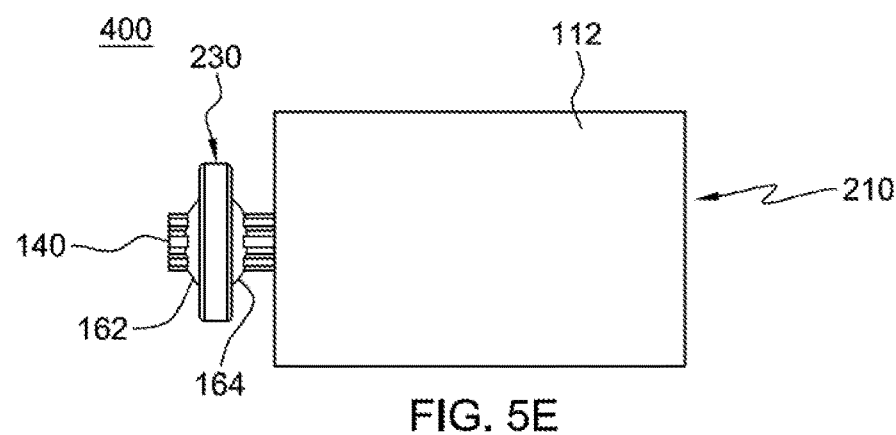
FIG. 5E is a side view of the spinal cage system of FIG. 5B, in accordance with an aspect of the present invention.

Another spinal cage system 200 is shown in FIGS. 2A-2F. The spinal cage system 200 may include a cage 210, an external plate 230, the rod 140, and the internal plate 150. The rod 140 and internal plate 150 may be of the type described above with reference to FIGS. 1A-1E. The cage 210 may be similar to the cage 110 and may include the body portion 112, at least one opening 114, the plurality of protrusions 116, and the first and second holes 120, 122 of the cage 110, as described in greater detail above with reference to FIGS. 1A-1E. The first and second holes 120, 122 are illustrated in greater detail in FIG. 2F, which shows a transparent cage 210. As shown in FIG. 2F, the first hole 120 may be angled in a first direction and the second hole 122 may be angled in a second direction, for example, the first hole 120 may be angled in a distal direction and the second hole 122 may be angled in a proximal direction. In addition, the cage 210 may include, in one embodiment, an opening 212 on the anterior surface of the cage 210. The opening 212 may be sized to receive the rod 140 and may also include a plurality of protrusions or teeth 214. Alternatively, the cage 210 may include opening 118, as discussed in greater detail above with reference to FIGS. 1A-1E, and a washer 216 may be, for example, press fit into the opening 118. The washer 216 may include an opening 212 and a plurality of protrusions or teeth 214. The opening 212 may be sized to receive the rod 140 and the plurality of protrusions 214 may be sized and positioned to fit into the plurality of grooves 146 in the rod 140 to prevent rotation of the rod 140. Alternatively, the plurality of protrusions 214 of the cage 210 may be sized to enable the rod 140 to rotate relative to the cage 210.

The external plate 230 may include an opening 232 and at least two holes 234 each extending from a top surface to a bottom surface of the external plate 230. The opening 232 may be sized to receive the rod 140. The at least two holes 234 may be, for example, holes for securing the external plate 230 to a patient's vertebral bodies using, for example, fasteners, such as bone screws. The at least two holes 234 may be positioned, for example, with one to a first side of the opening 232 and a second to a second side of the opening 232 opposite the first side. In the depicted embodiments of FIGS. 2A, 2B, and 2E, the at least two holes 234 include four holes, two to the first side of the opening 232 and two to the second side of the opening 232. Additional configurations for holes 234 are also contemplated in external plate 230 as desired by the surgeon for placing bone screws to secure the plate 230 to the patient's spine. The external plate 230 may have a length sized based on the surgical procedure being performed and the length may be, for example, approximately the same length as the cage 210, longer than the cage 210, or smaller than the cage 210.

The spinal cage system 200 may also include at least one locking mechanism 160, as shown in FIGS. 2B-2D. The at least one locking mechanism 160 may be of the type described above with reference to spinal cage system 100. The at least one locking mechanism 160 may be used to assemble the spinal cage system 200. For example, the spinal cage system 200 may be assembled by inserting the rod 140 into the opening 212 in the cage 210. Once the rod 140 is inserted into the cage 210, the internal plate 150 may be secured to the rod 140 using at least one locking mechanism 160 by, for example, sliding the top member 162 of the locking mechanism 160 onto the rod 140, then sliding the internal plate 150 onto the rod 140, and finally sliding the bottom member 164 of the locking mechanism 160 onto the rod 140. Next the top member 162 and bottom member 164 of the locking mechanism 160 may be secured together to hold the internal plate 150 to the rod 140. The top member 162 may be secured to the bottom member 164 by, for example, press fitting the top member 162 and the bottom member 164 together. Alternative locking mechanisms 160 are also contemplated. The external plate 230 may also be secured to the rod 140 using at least one locking mechanism 160. For example, a bottom member 164 of the locking mechanism 160 may be slid onto the rod 140, then the external plate 230 may be slid over the rod 140, and finally the top member 162 of the locking mechanism 160 may be slid over the rod 140. Next the top member 162 and bottom member 164 may be secured together to attach the external plate 230 to the rod 140. In one embodiment, after securing the external plate 230 to the rod 140, the external plate 230 may rotate relative to the rod 140 and in another embodiment rotation of the external plate 230 will cause rotation of the rod 140 and vice versa.

Referring now to FIGS. 4A-4E, another spinal cage system 300 is shown. The spinal cage system 300 may include the cage 210, the external plate 130, and the rod 140. The cage 210 may be of the type described above with reference to FIGS. 2A-2F and the external plate 130 and the rod 140 may be of the type described above with reference to FIGS. 1A-1E. The spinal cage system 300 may also include at least one locking mechanism 160, as described above with reference to FIGS. 1A-2F. In the embodiments depicted in FIGS. 4A-4E, there are two locking mechanisms 160 which include a top member 162 and a bottom member 164.

The spinal cage system 300 may be assembled prior to insertion into a patient by inserting the rod 140 through the opening 212 in the cage 210. After the rod is inserted through the opening 212 and is extending into the at least one opening 114 in the cage 210, a locking mechanism 160 may be attached to the second end 144 of the rod 140. The locking mechanism 160 may be attached by inserting a top member 162 over the second end 144 of the rod 140 in the opening 114. Next a bottom member 164 may be inserted over the second end 144 of the rod 140 and the top member 162 and bottom member 164 may be aligned near the second end 144 and secured together. When the top member 162 and bottom member 164 are secured together to form the locking mechanism 160, they also attach the locking mechanism 160 to the rod 140 to form a stop member 310. Alternatively, if the opening 118 includes a removable washer 216, the spinal cage system 300 may be assembled after insertion of the cage 210 into the patient. The washer 216 may have an opening shaped to match the shape of the rod 140 and to either allow for the rod 140 to rotate within the washer opening or fix the rod 140 in place. For example, the locking mechanism 160 may be fastened to the rod 140 to form the stop member 310, as described in greater detail above. Then, the stop member 310 may be inserted through opening 118 into cage 210. The opening 212 of the washer 216 may then be aligned with and inserted over the first end 142 of the rod 140 and secured into opening 118.

Once the stop member 310 is formed and positioned within the opening 114 in the cage 210, the external plate 130 may be attached to the rod 140 with a locking mechanism 160. The external plate 130 may be attached by inserting a bottom member 164 on the first end 142 of the rod 140, then sliding the external plate 130 over the rod 140, and finally sliding a top member 162 onto the rod 140. Next the top member 162 and bottom member 164 may be secured together to attach the external plate 130 to the rod 140. The external plate 130 may be secured to the rod 140 so that it may rotate relative to the rod 140 or the external plate 130 may be secured to the rod 140 so that as the external plate 130 is rotated the rod 140 will also rotate. The external plate 130 may be secured to the rod 140 either before or after the stop member 310 is secured to the second end 144 of the rod 140.

A spinal cage system 400 is shown in FIGS. 5A-5E. The spinal cage system 400 may include the cage 210, the external plate 230, and the rod 140. The cage 210 and the external plate 230 may be of the type described above with reference to FIGS. 2A-2F and the rod 140 may be of the type described above with reference to FIGS. 1A-1E. The spinal cage system 400 may also include at least one locking mechanism 160, as described above with reference to FIGS. 1A-2F. In the embodiments depicted in FIGS. 5A-5E, there are two locking mechanisms 160 which include a top member 162 and a bottom member 164.

The spinal cage system 400 may be assembled by inserting the rod 140 through the opening 212 in the cage 210. After the rod is inserted through the opening 212 and is extending into the at least one opening 114 in the cage 210, a locking mechanism 160 may be attached to the second end 144 of the rod 140. The locking mechanism 160 may be attached by inserting a top member 162 over the second end 144 of the rod 140 in the opening 114. Next a bottom member 164 may be inserted over the second end 144 of the rod 140 and the top member 162 and bottom member 164 may be aligned near the second end 144 and secured together. When the top member 162 and bottom member 164 are secured together to form the locking mechanism 160, they also attach the locking mechanism 160 to the rod 140 to form a stop member 410. Alternatively, if the opening 118 includes a removable washer 216, the spinal cage system 400 may be assembled after insertion of the cage 210 into the patient. For example, the locking mechanism 160 may be fastened to the rod 140 to form the stop member 410, as described in greater detail above. Then, the stop member 410 may be inserted through opening 118 into cage 210. The opening 212 of the washer 216 may then be aligned with and inserted over the first end 142 of the rod 140 and secured into opening 118.

Once the stop member 410 is formed and positioned within the opening 114 in the cage 210, the external plate 230 may also be attached to the rod 140 with a locking mechanism 160. The external plate 230 may be attached by inserting a bottom member 164 on the first end 142 of the rod 140, then sliding the external plate 230 over the rod 140, and finally sliding a top member 162 onto the rod 140. Next the top member 162 and bottom member 164 may be secured together to attach the external plate 230 to the rod 140. The external plate 230 may be secured to the rod 140 so that it may rotate relative to the rod 140 or the external plate 230 may be secured to the rod 140 so that as the external plate 230 is rotated the rod 140 will also rotate. The external plate 230 may be secured to the rod 140 either before or after the stop member 410 is secured to the second end 144 of the rod 140.

Referring now to FIGS. 6A-6E, a spinal cage system 500 is shown. The spinal cage system 500 includes the cage 210, an external plate 510, and the rod 140. The cage 210 may be of the type described above with reference to FIGS. 2A-2F and the rod 140 may be of the type described above with reference to FIGS. 1A-1E. The spinal cage system 500 may also include at least one locking mechanism 160, as described above with reference to FIGS. 1A-2F. In the embodiments depicted in FIGS. 6A-6E, there are two locking mechanisms 160 which include a top member 162 and a bottom member 164.

Figure 6A:
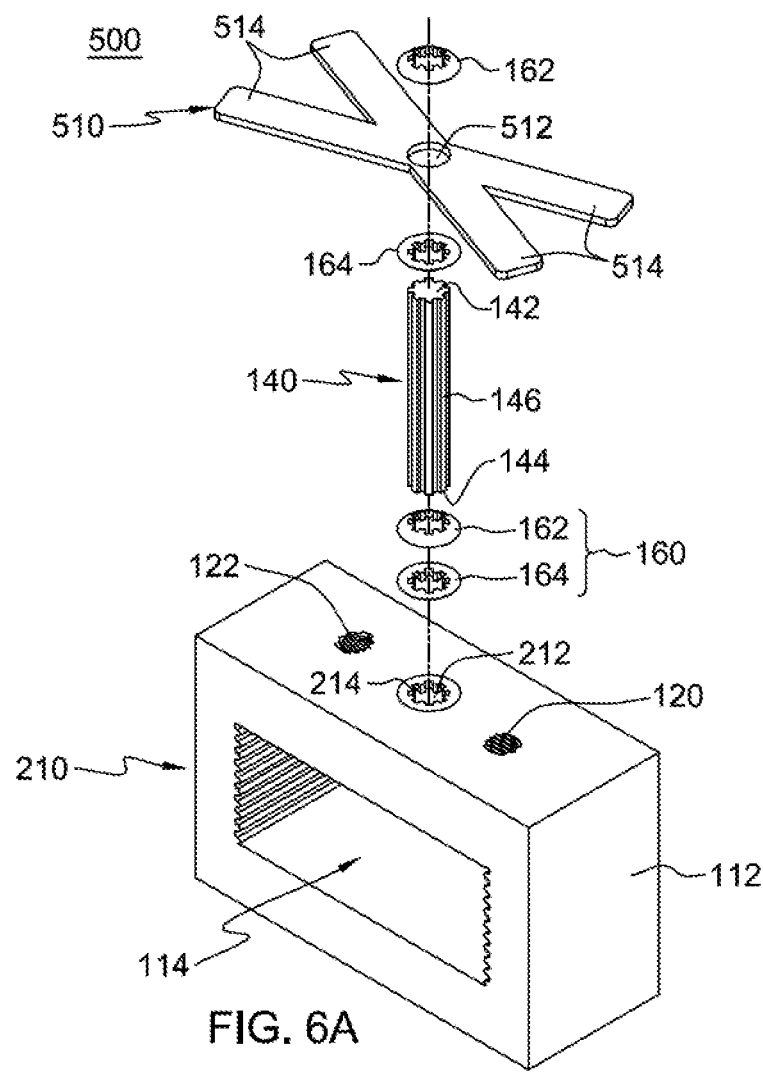
FIG. 6A is an exploded view of an embodiment of a spinal cage system, in accordance with an aspect of the present invention.
Figure 6B:
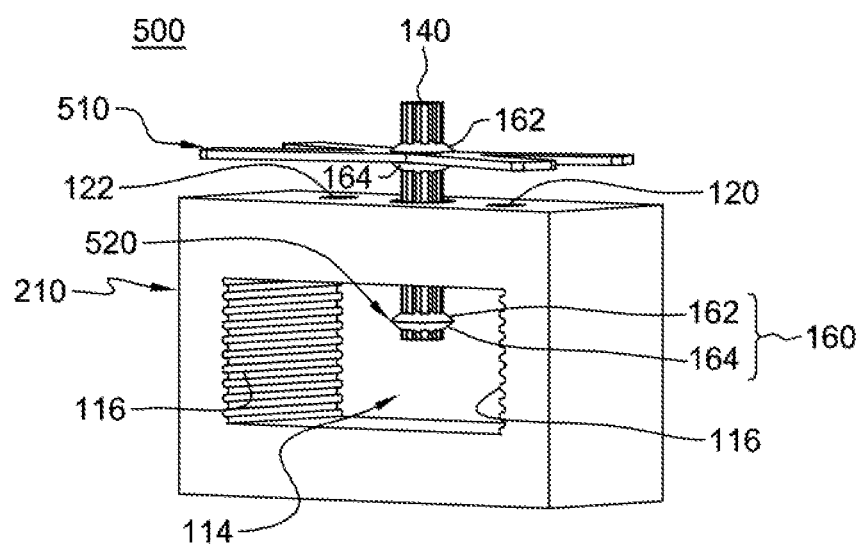
FIG. 6B is an isometric view of the assembled spinal cage system of FIG. 6A, in accordance with an aspect of the present invention.
Figure 6C:
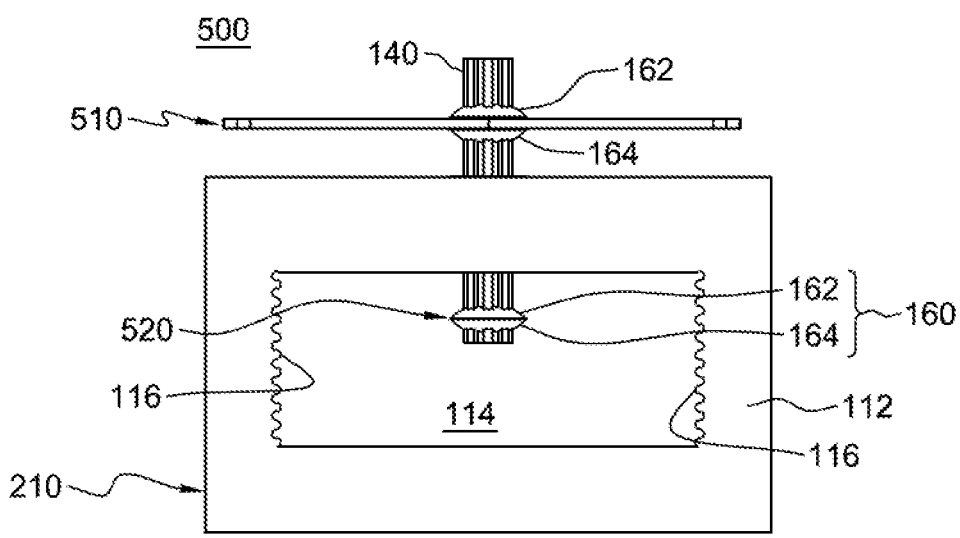
FIG. 6C is a top view of the spinal cage system of FIG. 6B, in accordance with an aspect of the present invention.
Figure 6D:
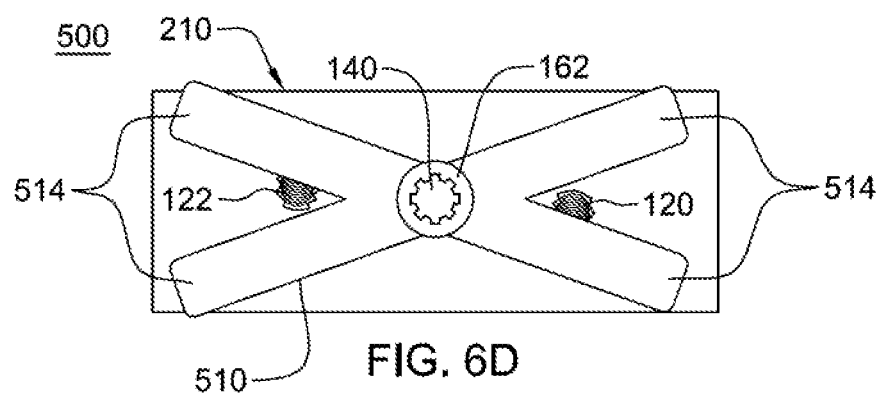
FIG. 6D is an anterior view of the spinal cage system of FIG. 6B, in accordance with an aspect of the present invention.
Figure 6E:
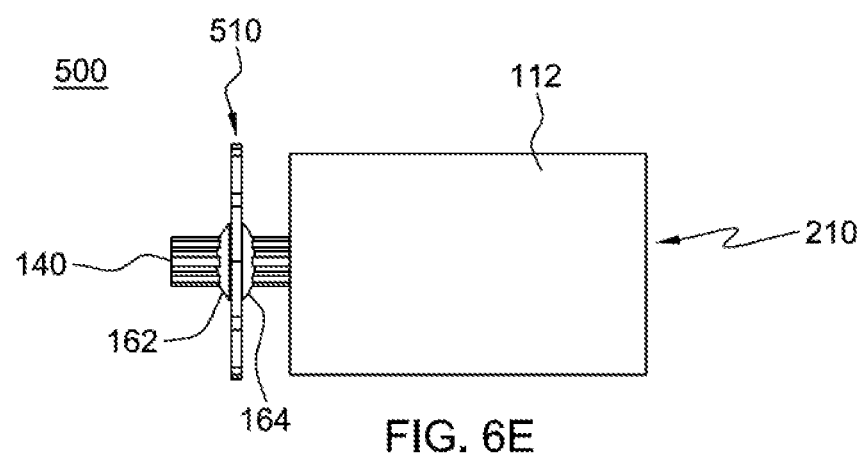
FIG. 6E is a side view of the spinal cage system of FIG. 6B, in accordance with an aspect of the present invention.

The external plate 510 may include an opening 512 and a plurality of extensions members 514. The opening 512 may be positioned, for example, in the center of the plurality of extension members 514. As shown in FIGS. 6A and 6D, the external plate 510 may include, for example, four extension members 514, although other numbers of extension members 514 are also contemplated. The extension members 514 may include, for example, at least one hole along each extension member 514 to receive a fastener for securing the external plate 510 to the vertebral bodies. It is also contemplated that at least two of the extension members 514 may include, for example, at least one hole along each extension member 514 for receiving fasteners to secure the external plate 510 to the vertebral bodies. The extension members 514 may also be used to, for example, prevent fastener or screw back out by aligning over the holes 120, 122. The external plate 510 may have a length sized based on the surgical procedure being performed and the length may be, for example, approximately the same length as the cage 210, longer than the cage 210, or smaller than the cage 210.

The spinal cage system 500 may be assembled by inserting the rod 140 through the opening 212 in the cage 210. After the rod is inserted through the opening 212 and is extending into the at least one opening 114 in the cage 210, a locking mechanism 160 may be attached to the second end 144 of the rod 140. The locking mechanism 160 may be attached by inserting a top member 162 over the second end 144 of the rod 140 in the opening 114. Next a bottom member 164 may be inserted over the second end 144 of the rod 140 and the top member 162 and bottom member 164 may be aligned near the second end 144 and secured together. When the top member 162 and bottom member 164 are secured together to form the locking mechanism 160, they also attach the locking mechanism 160 to the rod 140 to form a stop member 520. Alternatively, if the opening 118 includes a removable washer 216, the spinal cage system 500 may be assembled after insertion of the cage 210 into the patient. For example, the locking mechanism 160 may be fastened to the rod 140 to form the stop member 520, as described in greater detail above. Then, the stop member 520 may be inserted through opening 118 into cage 210. The opening 212 of the washer 216 may then be aligned with and inserted over the first end 142 of the rod 140 and secured into opening 118.

Once the stop member 520 is formed and positioned within the opening 114 in the cage 210, the external plate 510 may also be attached to the rod 140 with a locking mechanism 160. The external plate 510 may be attached by inserting a bottom member 164 on the first end 142 of the rod 140, then sliding the external plate 510 over the rod 140, and finally sliding a top member 162 onto the rod 140. Next the top member 162 and bottom member 164 may be secured together to attach the external plate 510 to the rod 140. The external plate 510 may be secured to the rod 140 so that it may rotate relative to the rod 140 or the external plate 510 may be secured to the rod 140 so that as the external plate 510 is rotated the rod 140 will also rotate. The external plate 510 may be secured to the rod 140 either before or after the stop member 520 is secured to the second end 144 of the rod 140.

A spinal cage system 600 is shown in FIGS. 7A-7E. The spinal cage system 600 includes the cage 210, an external plate 610, and the rod 140. The cage 210 may be of the type described above with reference to FIGS. 2A-2F and the rod 140 may be of the type described above with reference to FIGS. 1A-1E. The spinal cage system 600 may also include at least one locking mechanism 160, as described above with reference to FIGS. 1A-2F. In the embodiments depicted in FIGS. 7A-7E, there are two locking mechanisms 160 which include a top member 162 and a bottom member 164.

Figure 7C:
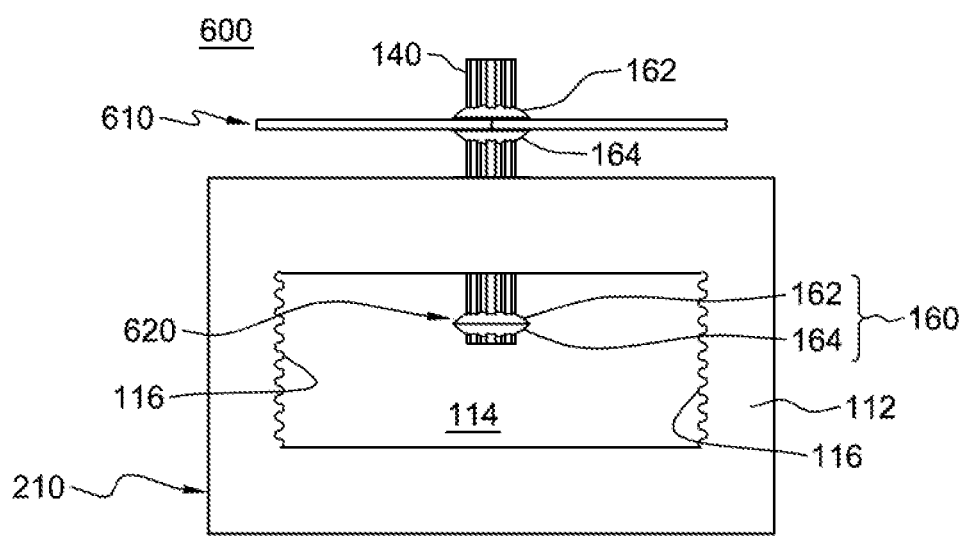
FIG. 7C is a top view of the spinal cage system of FIG. 7B, in accordance with an aspect of the present invention.
Figure 7D:
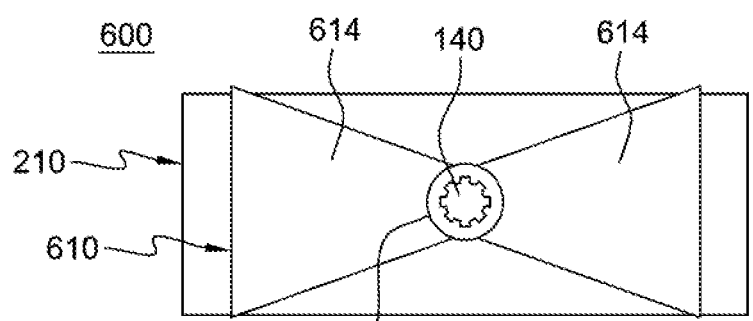
FIG. 7D is an anterior view of the spinal cage system of FIG. 7B, in accordance with an aspect of the present invention.
Figure 7E:
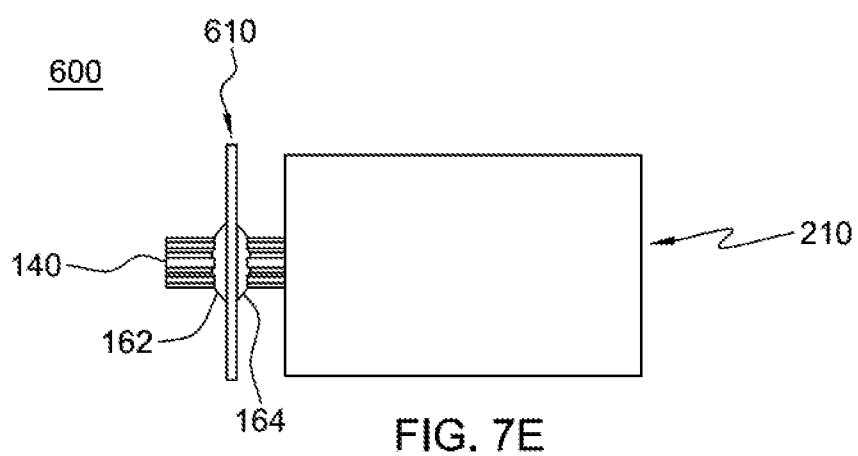
FIG. 7E is a side view of the spinal cage system of FIG. 7B, in accordance with an aspect of the present invention.

The external plate 610 may include an opening 612 and a plurality of extensions members 614. The opening 612 may be positioned, for example, in the center of the plurality of extension members 614. As shown in FIGS. 7A and 7D, the external plate 610 may include, for example, two extension members 614, although other numbers of extension members 614 are also contemplated. The extension members 614 may include, for example, at least one hole on each extension member 614 to receive a bone screw for securing the external plate 610 to the vertebral bodies. The extension members 614 may also be used to, for example, prevent back out of the fasteners by aligning over the holes 120, 122. The external plate 610 may have a length sized based on the surgical procedure being performed and the length may be, for example, approximately the same length as the cage 210, longer than the cage 210, or smaller than the cage 210.

The spinal cage system 600 may be assembled by inserting the rod 140 through the opening 212 in the cage 210. After the rod is inserted through the opening 212 and is extending into the at least one opening 114 in the cage 210, a locking mechanism 160 may be attached to the second end 144 of the rod 140. The locking mechanism 160 may be attached by inserting a top member 162 over the second end 144 of the rod 140 in the opening 114 and inserting a bottom member 164 over the second end 144 of the rod 140. The top member 162 and bottom member 164 may then be aligned near the second end 144 and secured together. When the top member 162 and the bottom member 164 are secured together to form the locking mechanism 160, they also attach the locking mechanism 160 to the rod 140 to form a stop member 620. The external plate 610 may also be attached to the rod 140 with a locking mechanism 160. The external plate 610 may be attached by inserting a bottom member 164 on the first end 142 of the rod 140, then sliding the external plate 610 over the rod 140, and finally sliding a top member 162 onto the rod 140. Next the top member 162 and bottom member 164 may be secured together to attach the external plate 610 to the rod 140. The external plate 610 may be, for example, secured to the rod 140 so that it may rotate relative to the rod 140. Alternatively, the external plate 610 may be secured to the rod 140 so that as the external plate 610 is rotated the rod 140 also rotates. The external plate 610 may be secured to the rod 140 either before or after the stop member 620 is secured to the second end 144 of the rod 140.

Figure 10:
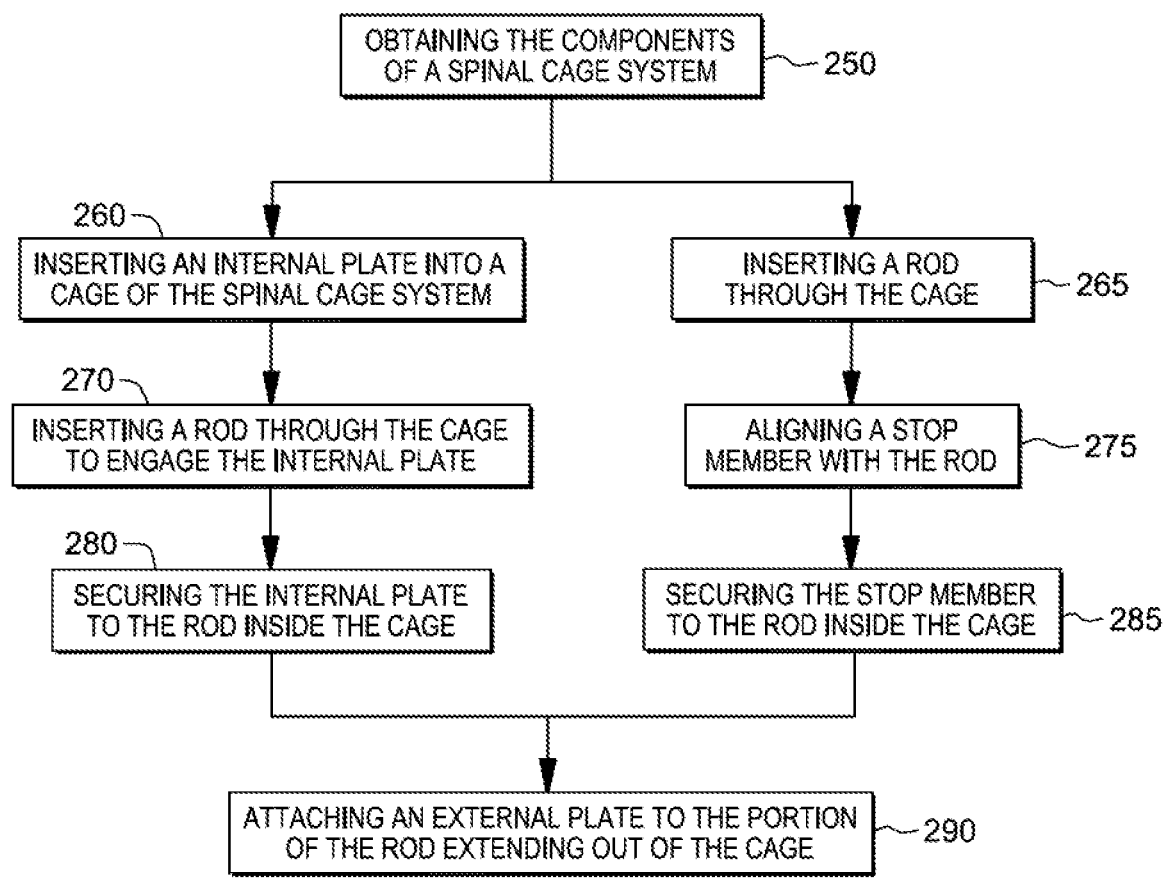
FIG. 10 depicts one embodiment of a method of assembling a spinal cage system, in accordance with an aspect of the present invention.

A method of assembling spinal cage systems 100, 200, 300, 400, 500, 600 is shown in FIG. 10. The method may include, for example, obtaining the components of a spinal cage system 250. The components of the spinal cage system may include, for example, a cage 110, 210, an external plate 130, 230, 510, 610, a rod 140, and at least one locking mechanism 160. In addition, some spinal cage systems may include an internal plate 150. In one embodiment the method may further include inserting an internal plate into the cage 260, inserting a rod through the cage to engage the internal plate 270, and securing the internal plate to the rod inside the cage 280. Alternatively, the method may further include inserting the rod through the cage 265, aligning a stop member with the rod 275, and securing the stop member to the rod inside the cage 285. Both methods may also include attaching an external plate to the portion of the rod extending out of the cage 290. The methods of assembling spinal cage systems 100, 200, 300, 400, 500, 600 are described in greater detail above.

Figure 11:
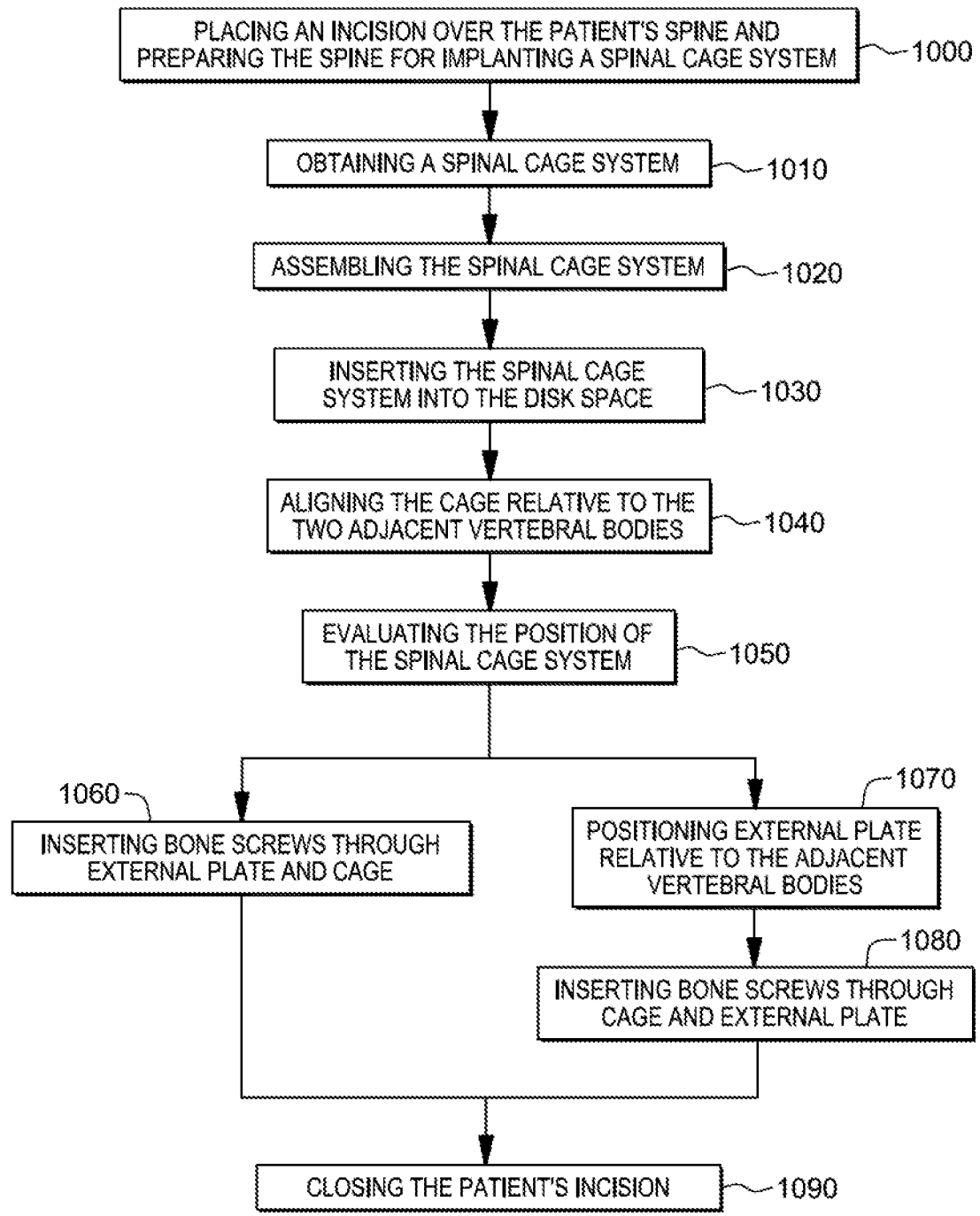
FIG. 11 depicts one embodiment of a method for inserting a spinal cage system, in accordance with an aspect of the present invention.

A method for inserting a spinal cage system 100, 200, 300, 400, 500, 600, 800, 900 is shown in FIG. 11. The method may include making an incision over the patient's spine and preparing the spine for implanting a spinal cage system 1000. The method may also include obtaining a spinal cage system 1010 and assembling the spinal cage system 1020. Further, the method may include inserting the spinal cage system into the disk space 1030 and aligning the cage into a desired position relative to the two adjacent vertebral bodies 1040. The method may also include evaluating the position of the spinal cage system 1050. If the placement of the spinal cage system and the alignment of the patient's spine are acceptable to the surgeon, then fasteners, such as bone screws, may be inserted through the external plate and the cage 1060, in the position shown in FIG. 9A. Alternatively, if the placement of the spinal cage system and/or alignment of the patient's spine is not acceptable to the surgeon, the surgeon may reposition the external plate and/or the internal plate relative to the cage and vertebral bodies 1070. The surgeon may reposition the external plate by sliding the plate and rod in an anterior-posterior direction until a desired depth of the external plate is achieved. Then the external plate may be rotated until a desired superior-inferior alignment of the external plate relative to the vertebral bodies is achieved. Once the external plate has reached a desired position, the surgeon may insert fasteners, such as bone screws, through both the cage and the external plate 1080. Finally, the patient's incision may be closed 1090. The spinal cage systems 100, 200, 300, 400, 500, 600, 800, and 900 may be implanted into a human or an animal.

The method of FIG. 11 may be described in greater detail with reference to FIGS. 9A-9B. As shown in FIGS. 9A-9B, after preparing the patient's spine for insertion of the implant 300, the surgeon may slide the cage 210 into the disk space between two adjacent vertebral bodies 102, 104. If necessary the surgeon may tamp the cage 210 into a recessed position in the disk space. When the cage 210 is inserted into the disk space the external plate 130 may be attached to the cage 210 or the external plate 130 may be attached after the cage 210 is inserted into the patient. In both methods, the external plate 130 may either be positioned flush to the cage 210 or positioned at an extended position away from the cage 210. When the cage 210 is placed in a recessed position relative to the vertebral bodies 102, 104, the plate 130 will generally be offset from the cage 210 to allow the plate 130 to clear the vertebral bodies 102, 104 when it is rotated relative to the cage 210.

If the external plate 130 is attached to the cage 210 during the initial implantation it will generally be aligned parallel with the cage 210, as shown in FIG. 9A. Once the cage 210 has been placed at the desired depth, it will be determined if the external plate 130 needs to be translated in an anterior-posterior direction relative to the cage 210. In circumstances where the external plate 130 does not need to be moved in an anterior-posterior direction, the cage 210 and external plate 130 may be secured to the vertebral bodies 102, 104 as illustrated in FIG. 9A. The cage 210 and external plate 130 may be secured by inserting fasteners, such as bone screws, not shown, first through the holes 134 in the external plate 130 and then through the first and second holes 120, 122, respectively, in the cage 210.

Alternatively, if the external plate 130 does need to be moved in an anterior-posterior direction, then the external plate 130 may be translated in an anterior-posterior position with the rod 140 relative to the cage 210 until a desired anterior-posterior position of the external plate 130 has been achieved. Once the desired anterior-posterior position has been achieved, the external plate 130 may be rotated relative to the cage 210 to enable the external plate 130 to be secured to the vertebral bodies 102, 104. As shown in FIG. 9B, the external plate 130 can be positioned perpendicular to the cage 210, in fact, the external plate 130 may rotate 360° and be positioned at any desired angle relative to the cage 210. Once the desired position of the cage 210 and the external plate 130 have been determined, fasteners 320, such as bone screws, may be inserted into the first and second holes 120, 122 to secure the cage 210 to the vertebral bodies 102, 104. In addition, fasteners 322, such as bone screws, may be inserted through holes 134 in the external plate 130 to secure the external plate 130 to the vertebral bodies 102, 104.

Alternatively, when an internal plate 150 isn't used and the external plate 130 is inserted after the cage 210, the cage 210 will be inserted and fixed to the vertebral bodies 102, 104, then the external plate 130 may be coupled to the rod 140 and inserted into the patient to engage the cage 210. After the external plate 130 and the rod 140 are inserted into the cage 210, the external plate 130 may be translated and rotated to a desired position and secured to the patient's vertebral bodies 102, 104.

In a further alternative method, the cage 210 with the rod 140 may be inserted into the patient. Once the cage 210 is positioned in a desired position, the rod 140 may be translated relative to the cage 210 to position the rod 140 at a desired position for attachment of the external plate 130. Next the external plate 130 may be attached to the first end of the rod 140 either in the desired position for attachment to the vertebral bodies 102, 104 or in the position easiest for the surgeon to attach the external plate 130 and then rotated to the desired position for attachment to the vertebral bodies 102, 104.

After the cage 210 and the external plate 130 have been secured to the vertebral bodies 102, 104, either together or separately, the surgeon may finish the surgical procedure and close the patient's incision.

The spinal cage systems 100, 200, 300, 400, 500, 600 may be assembled, for example, in situ. Thus, enabling a surgeon to insert the spinal cage systems 100, 200, 300, 400, 500, 600 by, for example, endoscopic or tubular means with the external plate 130, 230, 510, 610 aligned with the cage 110, 210. Then, once the spinal cage system 100, 200, 300, 400, 500, 600 is inserted through a small aperture, the surgeon may assemble or adjust the external plate 130, 230, 510, 610 with respect to the cage 110, 210 in situ.

Figure 8A:
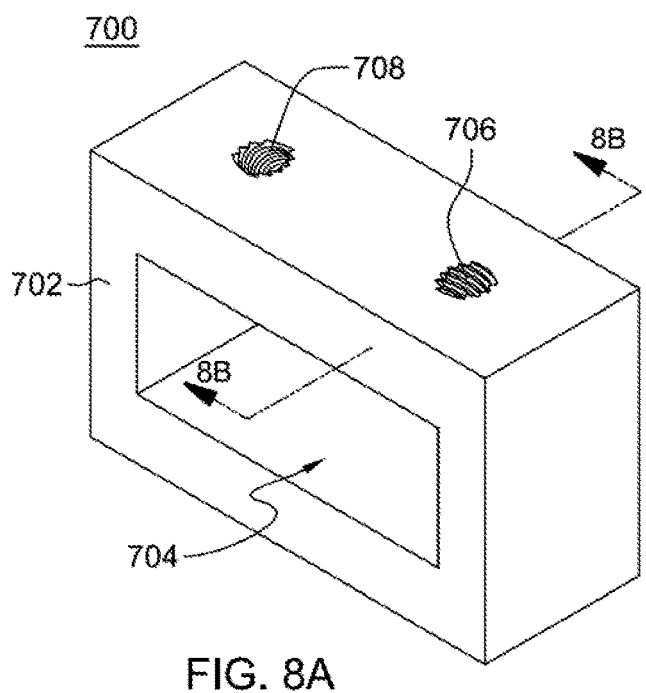
FIG. 8A is an isometric view of an embodiment of a spinal cage, in accordance with an aspect of the present invention.

A cage system 700 is shown in FIGS. 8A-8I. The cage system 700 includes, for example, a cage body portion 702, a locking member 710, and a fastener 730. The cage body portion 702 may include at least one opening 704 through the cage 702 to, for example, allow for bone fusion between two adjacent vertebral bodies in the spine. The at least one opening 704, as shown in FIG. 8A, extends from a superior surface to an inferior surface of the cage body portion 702. It is also contemplated that the at least one opening 704 may be positioned in an alternative position such that it extends from a first side to a second side of the cage body portion 702, an anterior surface to a posterior surface, and/or between any combination of the surfaces of the cage 702 to allow for insertion of bone graft material into the opening 704. The at least one opening 704 may be of the type described above with reference to the at least one opening 114 of FIGS. 1A-1E.

Figure 8B:
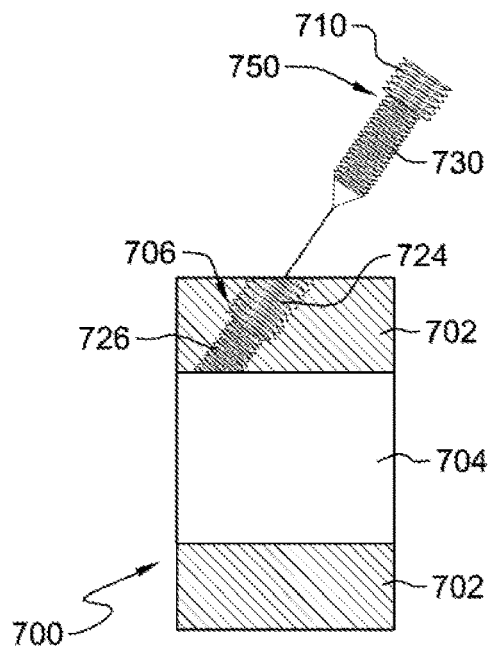
FIG. 8B is a cross-section of the spinal cage of FIG. 8A taken along line 8B-8B, in accordance with an aspect of the present invention.

The cage body portion 702 may also include at least one first hole 706 and at least one second hole 708, as shown in FIGS. 8A-8B. FIG. 8B shows a cross-section of the first hole 706. The first hole 706 may be angled, for example, toward the proximal surface of the cage body portion 702 and the second hole 708 may be angled, for example, toward the distal surface of the cage body portion 702. Alternative arrangements for the holes 706, 708 are also contemplated as discussed above in greater detail with respect to FIGS. 1A-1E. The holes 706, 708 may include a first section 724 and a second section 726. The first section 724 may have a larger diameter than the second section 726. In addition, the first section 724 and the second section 726 may be threaded.

Figure 8C:
FIG. 8C is a top view of a locking member, in accordance with an aspect of the present invention.
Figure 8F:
FIG. 8F is a top view of a fastener, in accordance with an aspect of the present invention.
Figures 8D, 8E:
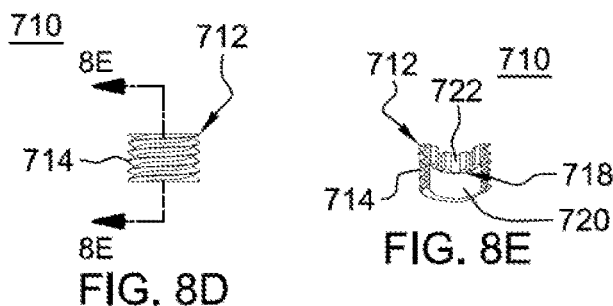
FIG. 8D is a side view of the locking member of FIG. 8C, in accordance with an aspect of the present invention.
FIG. 8E is a cross-section of the locking member of FIG. 8D taken along line 8E-8E, in accordance with an aspect of the present invention.

As shown in FIGS. 8C-8E, the locking member 710 may include a body or head 712 with an opening 716 that extends from a top to a bottom of the body 712. The opening 716 may create an interior surface 718. The interior surface 718 may include a smooth portion 720 and a grooved portion 722. As shown in FIG. 8E, the grooved portion 722 may be, for example, positioned near the top of the interior surface 718, while the smooth portion 720 may be positioned near the bottom of the interior surface 718. The grooved portion 722 may include a plurality of protrusions or teeth alternating with a plurality of grooves. The locking member 710 may also, for example, be press fit into the holes 706, 708 of the body portion 702. Thus, the cage system 700 would come preassembled with a locking member 710 fixed into each of the holes 706, 708. The locking mechanisms 710 would be fixed into the first sections 724 of the holes 706, 708.

Figure 8G:
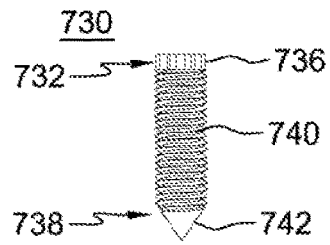
FIG. 8G is a side view of the fastener of FIG. 8F, in accordance with an aspect of the present invention.
Figure 8H:
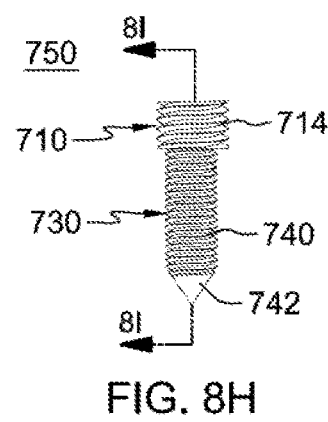
FIG. 8H is a side view of a bone screw assembly, in accordance with an aspect of the present invention.
Figure 8I:
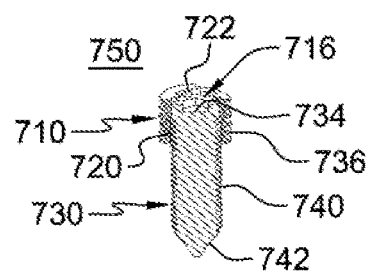
FIG. 8I is a cross-section of the bone screw assembly of FIG. 8H taken along line 8I-8I, in accordance with an aspect of the present invention.

The fastener 730, for example, a bone screw, is shown in FIGS. 8F-8G. The fastener 730 may include a head portion 732 and a shaft portion 738 extending away from the head portion 732. The head portion 732 may include an opening 734 and a plurality of grooves 736. The opening 734 may be positioned in the center of the head portion 732 to receive an instrument, for example, a drill or screw driver, for inserting the fastener 730 into the patient's vertebral bodies. The plurality of grooves 736 may be positioned around the exterior surface of the head portion 732 and designed to engage the grooved portion 722 of the locking member 710, as shown in FIG. 8I. The shaft portion 738 may include threads 740 and a tip 742. The threads 740 may be positioned on at least a portion of the exterior surface of the shaft portion 738. As shown in FIGS. 8G-8I, the threads 740 may, for example, extend from the head portion 732 to the tip 742 of the shaft portion 738.

As shown in FIGS. 8H-8I, the locking member 710 and the fastener 730 together may form a locking screw assembly 750. The plurality of grooves 736 of the fastener 730 may be positioned under the plurality of grooves of the locking member 710 to secure the fastener 730 into the patient's vertebral bodies and prevent back out of the fastener 730. Alternatively, the locking member 710 and fastener 730 may be coupled by the plurality of grooves 736 of the head portion 732 of the fastener 730 being aligned with the grooved portion 722 of the locking member 710, such that if the fastener 730 started to back out of the patient's bone the fastener 730 would engage the grooved portion 722 of the locking member 710 and prevent back out of the fastener 730. By coupling the locking member 710 and the fastener 730, the fastener 730 is prevented from turning and thereby prevents the fastener 730 from backing out of the patient's vertebral bodies. As shown in FIG. 8B, the fastener 730 is sized to engage and potentially couple to the second section 726 of the holes 706, 708 and the locking member 710 is sized to engage and potentially couple to the first section 724 of the holes 706, 708. The first and second sections 724, 726 of the holes 706, 708 may each be, for example, threaded to receive corresponding threads of the locking member 710 and fastener 730 and the threads may assist with preventing back out of the screw assembly 750. The cage system 700 may be implanted into a human or an animal. It is also contemplated that the locking screw assembly 750 may be used anywhere a bone fastener or screw is currently used, not only within a patient's spine, but anywhere in a patient's body in order to prevent back out of the fastener or screw from a bone. The locking member 710 and/or fastener 730 may also be used with the cages 110, 210 and may be, for example, secured into the holes 120, 122 by, for example, corresponding threads, press fitting, or any other securement method. Further, the locking members 710 may be inserted into the holes of the external plates, for example, into holes 134, 234 of the external plates 130, 230, to prevent the fasteners from backing out of the external plates after insertion into the patient's vertebral bodies.

Figure 12:
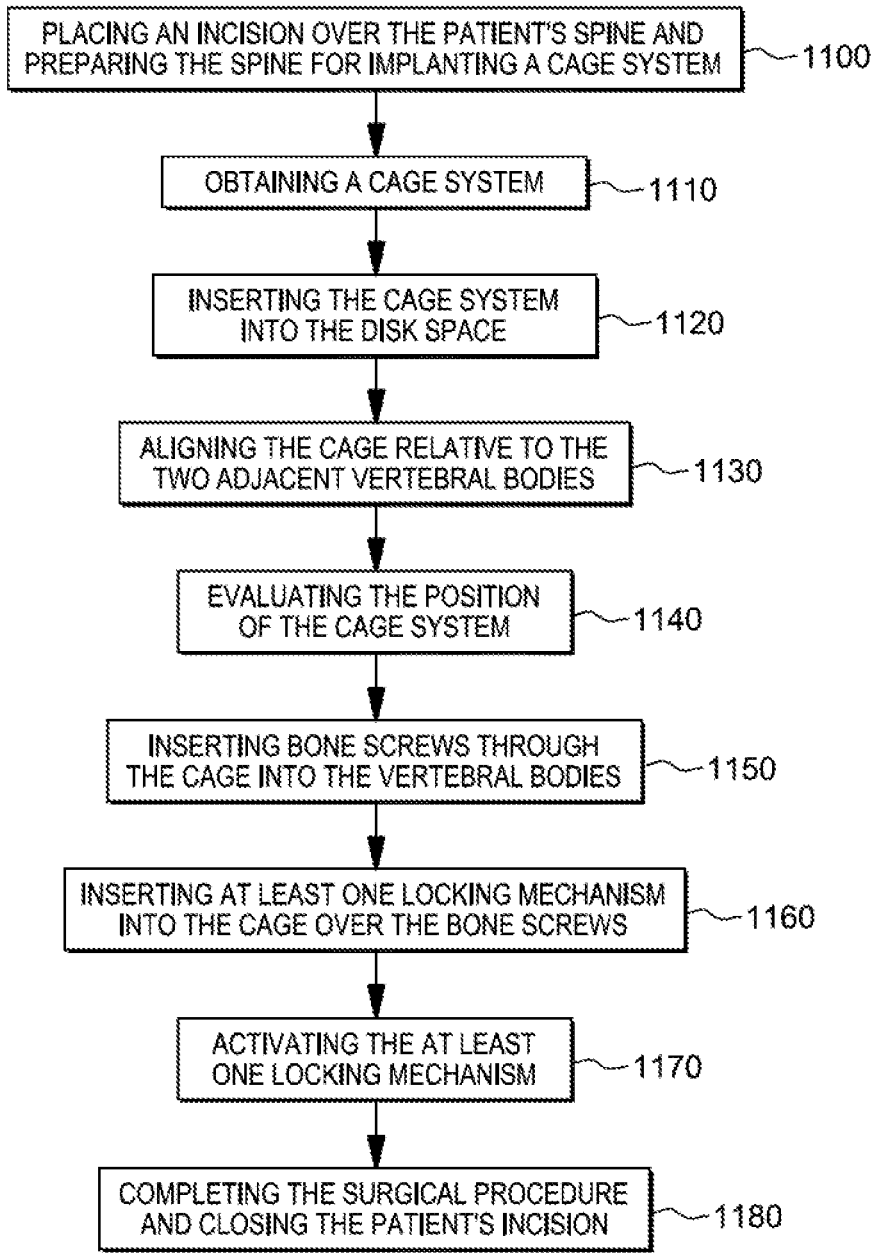
FIG. 12 depicts one embodiment of a method for inserting a cage system into a patient's spine, in accordance with an aspect of the present invention.

A method of inserting the cage system 700 is shown in FIG. 12. The method may include, for example, placing an incision over the patient's spine and preparing the spine for implanting a cage system 1100. The method may also include obtaining a cage system 1110 and inserting the cage system into the disk space 1120. The method may further include aligning the cage relative to the two adjacent vertebral bodies 1130 and evaluating the position of the cage system 1140. In addition, the method may include inserting fasteners through the cage and into the vertebral bodies 1150 and inserting at least one locking mechanism into the cage over the fasteners 1160. The method may also include activating the at least one locking mechanism to prevent the fasteners from backing out of the cage 1170. Finally, the method may include completing the surgical procedure and closing the patient's incision 1180.

Alternatively, if the cage system 700 includes integrated locking members 710 in holes 706, 708, then the method for inserting the cage system 700 may include, for example, placing an incision over the patient's spine and preparing the spine for implanting the cage system 700. The method may also include obtaining a cage system 700 with integrated locking members 710 and inserting the cage system 700 into the disk space. The method may further include aligning the cage relative to the two adjacent vertebral bodies and evaluating the position of the cage system 700. Further, the method may include inserting fasteners 730 through the locking members 710 and the body portion 702 and into the vertebral bodies. In addition, the method may include misaligning the head portion 732 of the fastener 730 with respect to the locking members 710 to block the fasteners 730 from backing out of the body portion 702.

The cage system 700 of FIGS. 8A-8I may also include an opening (not shown), such as opening 118 of the cage 110, as shown in FIGS. 1A-1B, or opening 212 of the cage 210, as shown in FIGS. 2A-2B, in the body portion 702 for receiving a rod 140 as described in greater detail above. Inserting an opening (not shown) in the body portion 702 enables use of an external plate, for example, external plate 130, 170, 230, with the cage system 700. In an embodiment of cage system 700 including an opening in the body portion 702, it may be assembled by obtaining the body portion 702 including an opening (not shown), inserting a rod 140 through the opening (not shown), and attaching a stop member, for example, stop member 310, 410, 520, or the like, or an internal plate, for example, internal plate 150 or the like, to the second end 144 of the rod 140 inside the at least one opening 704. Next the external plate 130, 170, or 230 may be attached to the first end 142 of the rod 140 by, for example, a locking mechanism 160 which enables the external plate 130, 170, or 230 to rotate relative to the rod 140.

If the cage system 700 includes an opening in the body portion 702 for receiving a rod 140, then the method as described above with reference to FIG. 12, may also include inserting the rod 140 into an opening (not shown) in the body portion 702 and securing a stop member, for example, stop member 310, 410, 520, or the like, or an internal plate, for example, internal plate 150 or the like, to the second end 144 of the rod 140 inside the at least one opening 704 prior to inserting the body portion 702 into the patient. An external plate, for example, external plate 130, 170, 230 or the like, may be rotatably attached to the rod 140 at a first end 142 prior to insertion of the body portion 702 into the patient. Alternatively, the external plate, for example, external plate 130, 170, 230 or the like, may be secured to the rod 140 at a first end 142 after the body portion 702 with the rod 140 and stop member or internal plate are inserted into the patient between two vertebral bodies. Once the body portion 702 and the rod 140 with the attached external cage are positioned between the two vertebral bodies, the surgeon may secure the external plate and body portion 702 to the vertebral bodies. The body portion 702 may be secured to the vertebral bodies with the external plate positioned parallel to the longitudinal axis of the body portion 702 by inserting a fastener through the openings in the external plate and the holes 706, 708 in the body portion 702.

Alternatively, the body portion 702 may be secured to the vertebral bodies with the external plate positioned out of alignment with the longitudinal axis of the body portion 702. For example, the external plate may be positioned relatively perpendicular to the longitudinal axis of the body portion 702 or in any position where the openings in the external plate are not aligned with the holes 706, 708 of the body portion 702. The external plate may be positioned to avoid prior instrumentation. This enables the surgeon to insert the body portion 702 deeper into the vertebral bodies and to adjust the depth of the external plate with respect to the body portion 702 by pulling the rod 140 out of the cage the required distance to enable the external plate to align with the surface, for example, anterior surface, of the vertebral bodies. Once the desired position of the body portion 702 between the vertebral bodies and the external plate with respect to the surface of the vertebral bodies is achieved then the body portion 702 and external plate may be secured to the vertebral bodies. When the external plate is not aligned with the holes 706, 708 of the body portion 702, then the fasteners 730 may be inserted into the holes 706, 708 to secure the body portion 702 to the vertebral bodies and locking members 710 may be inserted into holes 706, 708 to prevent the fasteners 730 from backing out of the vertebral bodies. The external plate may also be secured to the vertebral bodies using fasteners 730 and locking members 710 to prevent the fasteners 730 from backing out of the vertebral bodies. Alternative methods of inserting locking members 710 and fasteners 730 may also be used here as described above in greater detail. Once the locking members 710 have been activated to prevent the fasteners 730 from backing out the surgeon may complete the surgical procedure and close the patient's incision.

Another spinal cage system 800 is shown in FIGS. 13A-13E. The spinal cage system 800 may include a cage 810, the external plate 130, a rod 840, and a flange member 850. The external plate 130 may be of the type described above with reference to FIGS. 1A-1E, which will not be described again here for brevity sake. The cage 810 may be similar to the cage 110 and may include the body portion 112, at least one opening 114, the plurality of protrusions 116, the opening 118, and the first and second holes 120, 122 of the cage 110, as described in greater detail above with reference to FIGS. 1A-1E. As depicted, the cage 810 may have, for example, a different inner and outer configuration than the cage 110 to allow for engagement of the flange member 850 with the plurality of protrusions 116.

The rod 840, as shown in FIGS. 13A-13D, may include a first end 842 and a second end 844. The rod 140 may also include an opening 846 near the second end 844 of the rod 840 for receiving or coupling to the flange member 850. Alternative embodiments of the rod 140 are also contemplated including, but not limited to, a grooved rod, a threaded rod, a screw, or a combination of any of these. For example, the rod 840 may include at least one smooth portion and at least one threaded or grooved portion. The rod 840 may be sized to be received in opening 118 of the cage 810 and to allow for the rod to slide in an anterior/posterior direction within the cage 810 both prior to and after insertion into a patient. The rod 840 may also be sized to either allow for rotation of the rod 840 within the opening 118 of the cage 810 or to fix the rod 840 from rotating within the opening 118 of the cage 810. In addition, the rod 840 may be sized to be received in the opening 132 in the external plate 130. The rod 840 may be made of, for example, a metal material, such as titanium, nickel, or the like, or alternatively a metal alloy, such as nitinol or the like.

Referring now to FIGS. 13A-13E, the flange member 850 may include a first flange 852, a second flange 854, and a connecting member 856 attached at a first end to the first flange 852 and at a second end to the second flange 854. The first flange 852 may be positioned relatively perpendicular to the connecting member 856 in a first direction and the second flange 854 may be positioned relatively perpendicular to the connecting member 856 in a second direction. The first and second directions may be opposite each other such that the first and second flanges 852, 854 are parallel to each other at the points of attachment to the connecting member 856. The connecting member 856 may be sized to be received within the opening 846 in the rod 840. In one embodiment, the connecting member 856 may be rotatable within the opening 846, while in alternative embodiments, the connecting member 856 may be fixed within the opening 846. To allow for insertion of the flange member 850 into the opening 846 in the rod 840, the flange member 850 may be, for example, made of multiple pieces that couple together after insertion of at least a portion of the connecting member 856 into the opening 846. Alternatively, the connection between at least one of the first flange 852 and the connecting member 856 and the second flange 854 and the connecting member 856 may be hinged to allow for at least one of flanges 852, 854 to be aligned with the connecting member 856 for insertion through opening 846. Once the connecting member 856 is positioned in the opening 846, the at least one flange 852, 854 would be rotated and locked into place perpendicular to the connecting member 856.

Figure 13A:
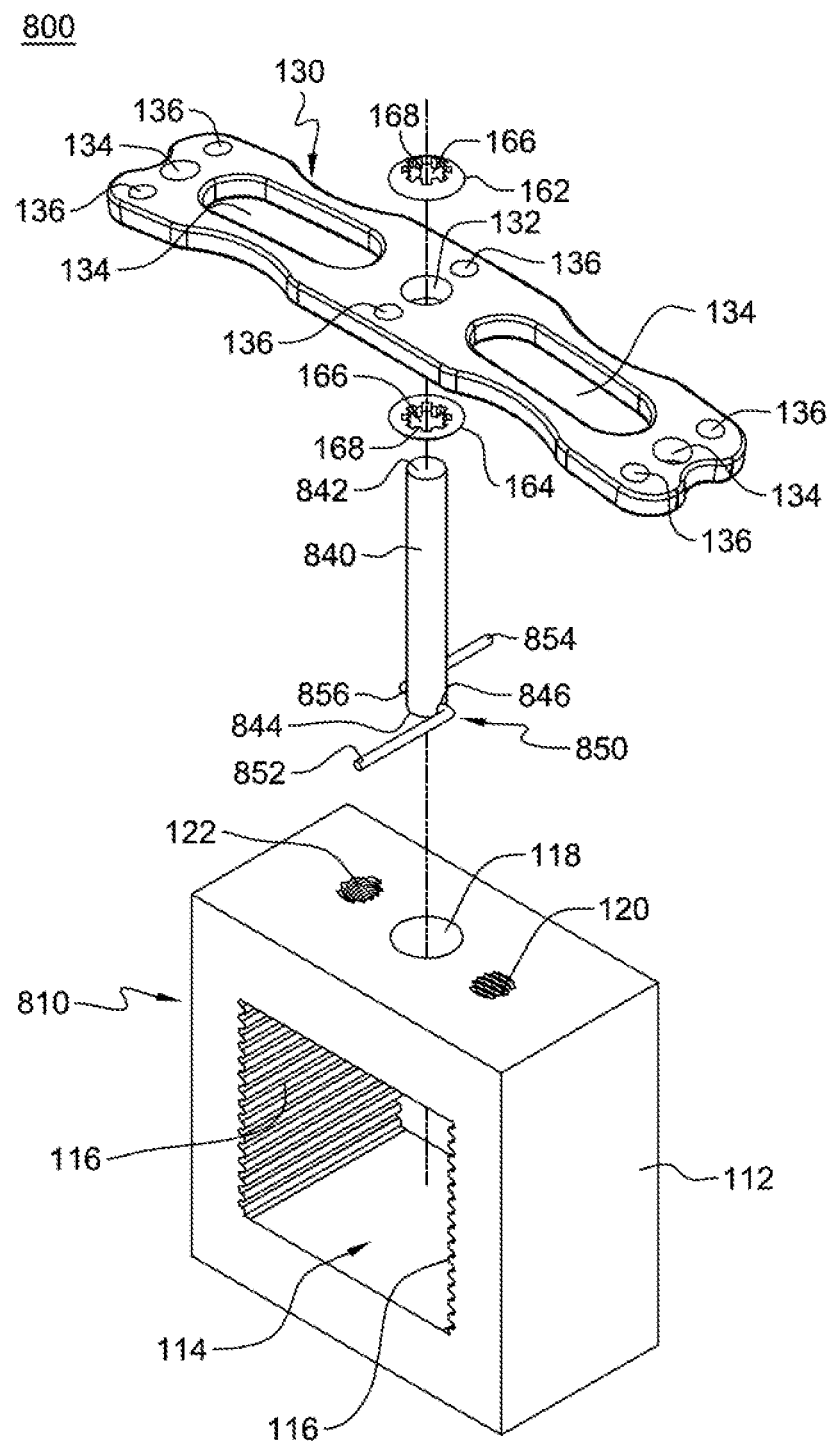
FIG. 13A is an exploded view of an embodiment of a spinal cage system, in accordance with an aspect of the present invention.
Figure 13B:
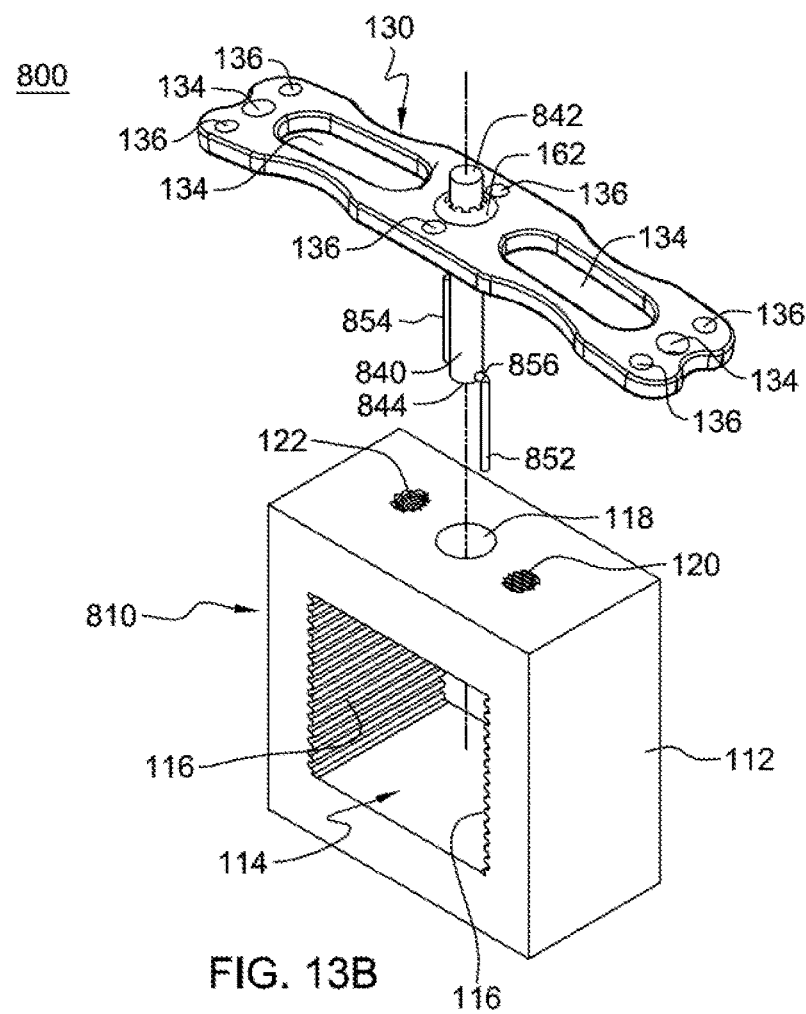
FIG. 13B is a partially exploded view of the spinal cage system of FIG. 13A in a position for insertion into a patient, in accordance with an aspect of the present invention.
Figure 13C:
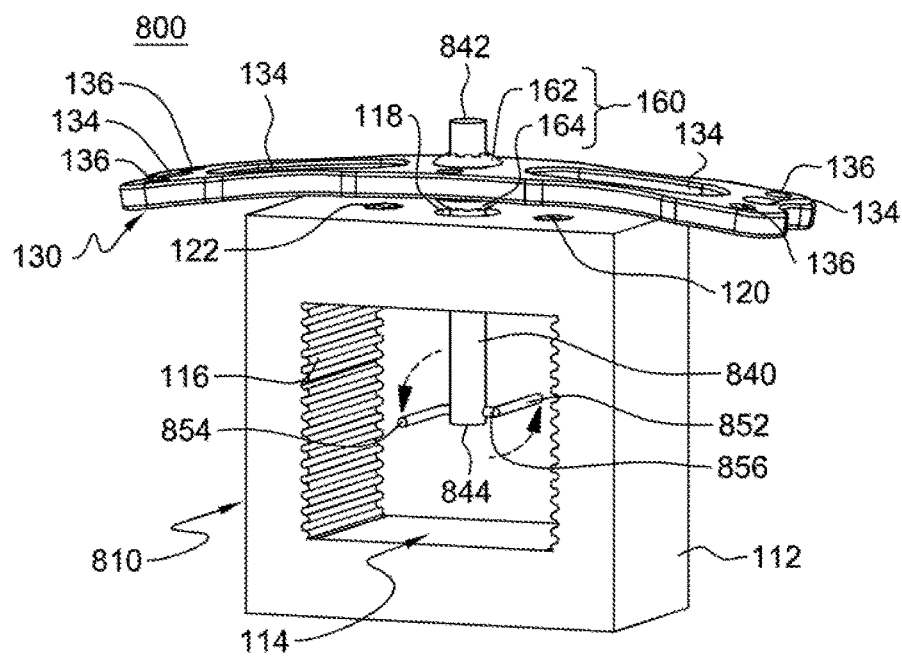
FIG. 13C is a perspective view of the assembled spinal cage system of FIG. 13A in a first position, in accordance with an aspect of the present invention.
Figure 13D:
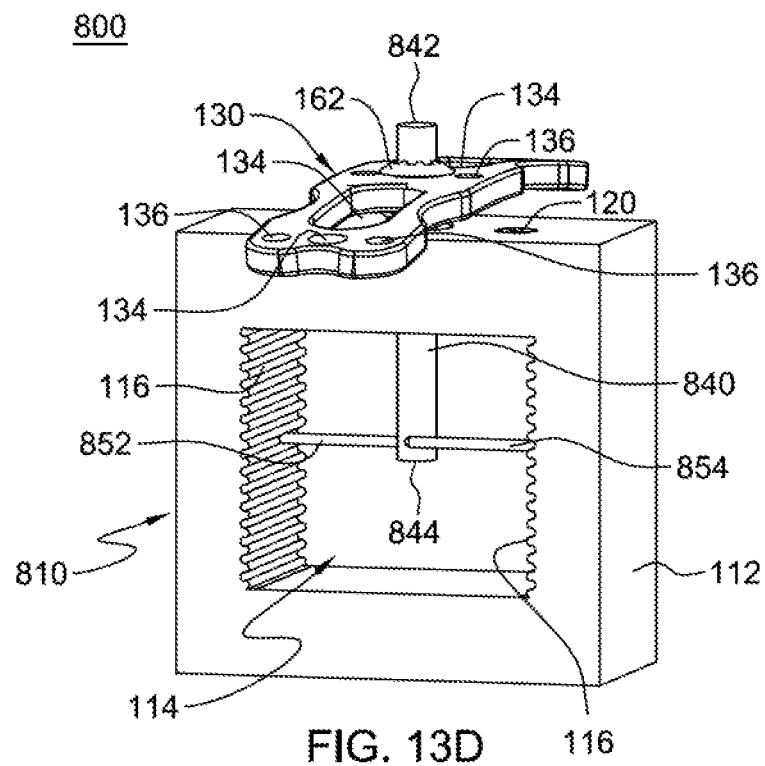
FIG. 13D is a perspective view of the assembled spinal cage system of FIG. 13A in a second position, in accordance with an aspect of the present invention.
Figure 13E:
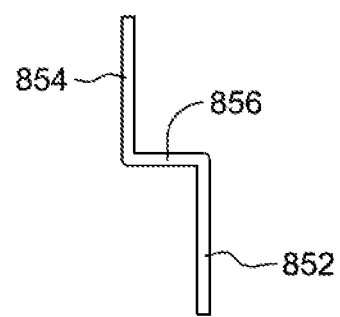
FIG. 13E is a side view of the flange member of the spinal cage system of FIG. 13A, in accordance with an aspect of the present invention.

The spinal cage system 800 may also include at least one locking mechanism 160, as shown in FIGS. 13B-13D. The at least one locking mechanism 160 may be of the type described above with reference to spinal cage system 100. The at least one locking mechanism 160 may be used to assemble the spinal cage system 800. For example, the spinal cage system 800 may be assembled by obtaining a coupled rod 840 and flange member 850, then rotating the flange member 850 parallel to the rod 840. Next, the end of the rod 840 with the flange member 850 may be inserted into the opening 118 in the cage 810, as shown in FIG. 13B. Once the rod 840 is inserted into the cage 810, the flange member 850 may be rotated to a position perpendicular to the rod 840, as shown in FIG. 13C. The flange member 850 may be rotated once positioned in opening 114 by, for example, weighting the flanges 852, 854 to allow for the flange member 850 to rotate once inside the cage 810. Alternatively, the rod 840 may include a channel (not shown) that extends from the first end 842 to the opening 846 to enable a surgeon to insert a tool or instrument into the channel to rotate the connecting member 856 and in turn rotate the flanges 852, 854 either perpendicular to or parallel with the rod 840.

The external plate 130 may be attached to the rod 840 prior to insertion of the flange member 850 into the cage 810 or alternatively after the flange member 850 is inserted into the cage 810. The external plate 130 may be attached to the rod 840 using at least one locking mechanism 160, as shown in FIGS. 13B-13D. For example, a bottom member 164 of the locking mechanism 160 may be slid onto the rod 840, then the external plate 130 may be slid over the rod 840, and finally the top member 162 of the locking mechanism 160 may be slid over the rod 840. Next, the top member 162 and bottom member 164 may be secured together to attach the external plate 130 to the rod 840. Once the external plate 130 is secured to the rod 840 and the cage 810 is positioned between the patient's vertebrae, the surgeon may move the external plate 130 in an anterior-posterior direction until the desired alignment with the adjacent vertebrae is achieved. Then, the surgeon may rotate the external plate 130 which will in turn rotate the rod 840 and coupled flange member 850. The flanges 852, 854 of the flange member 850 will rotate and each engage at least one of the plurality of protrusions 116 on opposite side walls of the cage 810, as shown in FIG. 13D. In another embodiment, the plate 130 may be configured to rotate independently of the rod 840, to allow the surgeon to rotate the rod 840 to secure the flanges 852, 854 each in a protrusion 116 to maintain the desired anterior-posterior position, while also providing the surgeon additional flexibility for positioning the external plate 130 on the patient's vertebrae. Once the external plate 130 and cage 810 are in the desired position, fasteners (not shown), for example, bone screws, may be inserted into the first and second holes 120, 122 to secure the cage 810 to the patient's adjacent vertebral bodies. In addition, fasteners (not shown), such as bone screws, may be inserted through the holes 134 in the external plate 130 to secure the external plate 130 to the patient's vertebral bodies.

Figure 14A:
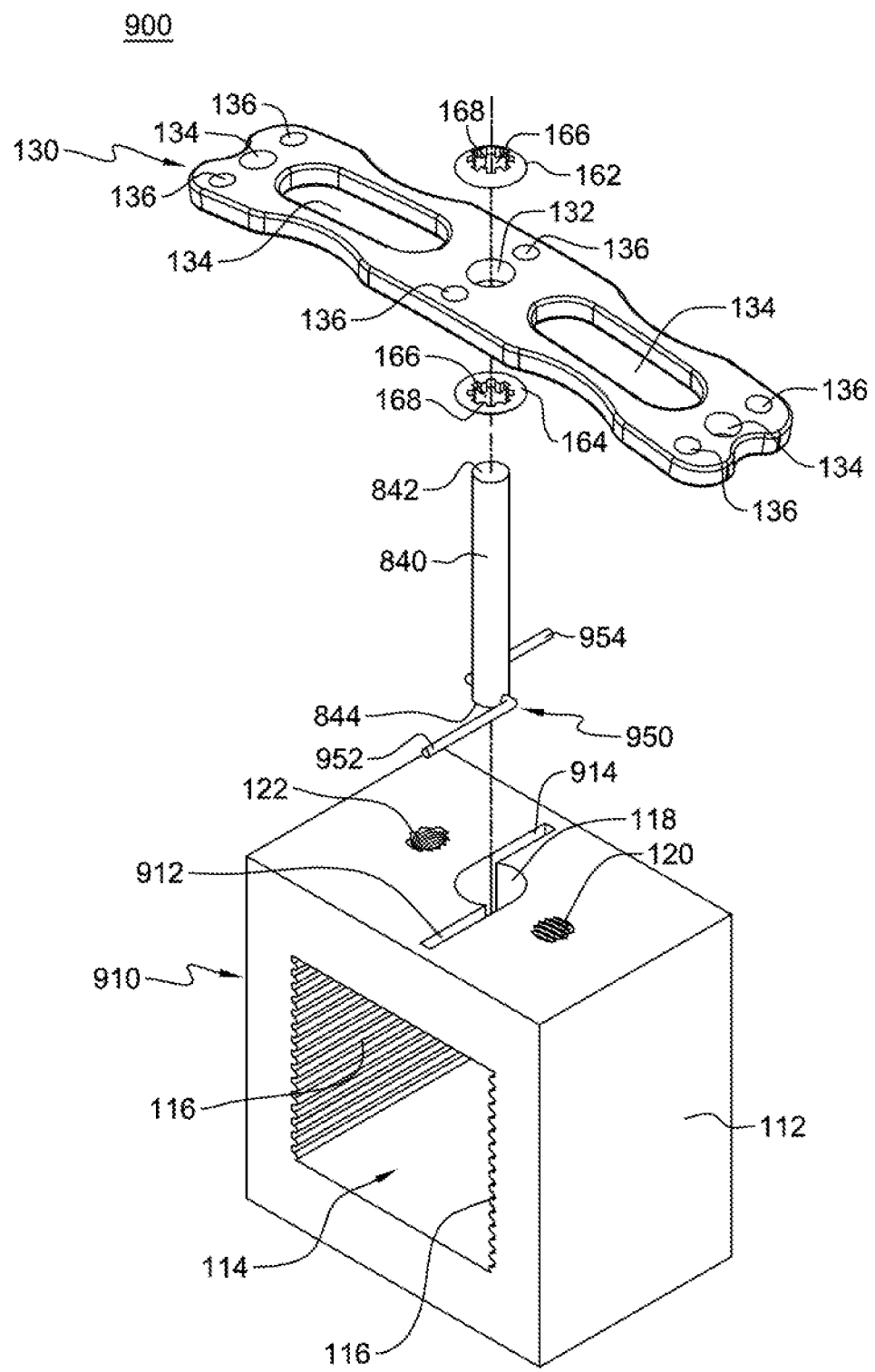
FIG. 14A is an exploded view of another embodiment of a spinal cage system, in accordance with an aspect of the present invention.
Figure 14B:
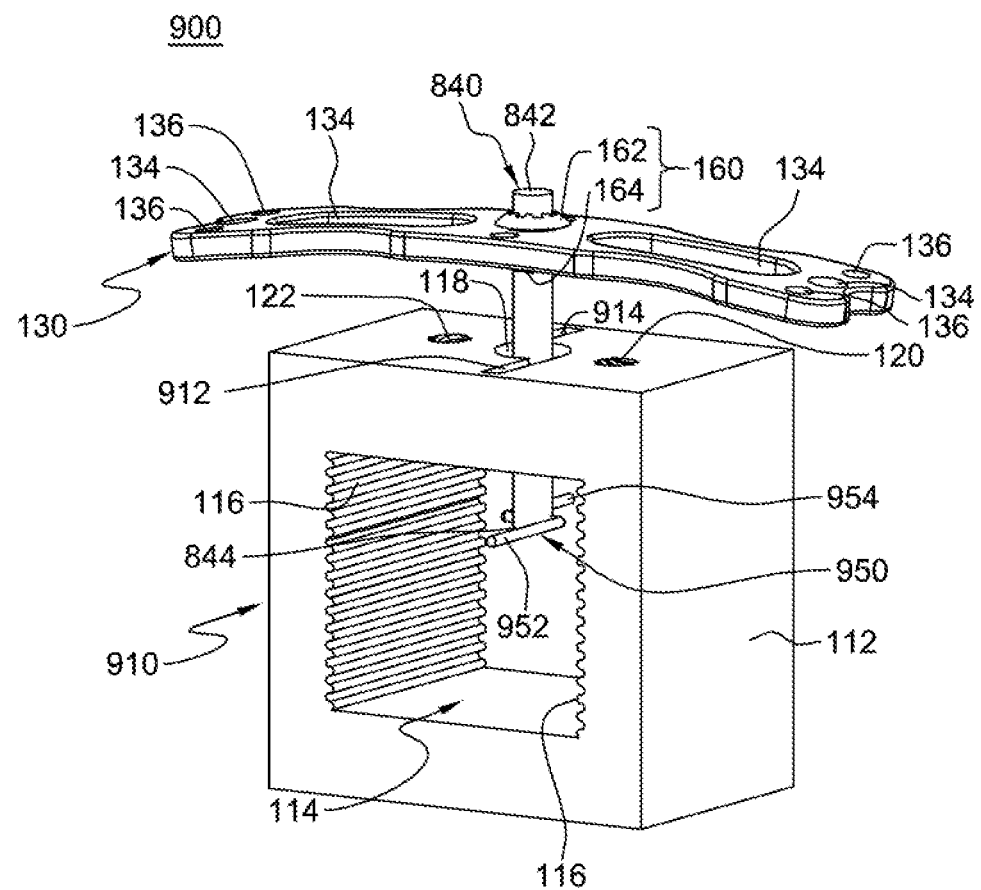
FIG. 14B is a perspective view of the assembled spinal cage system of FIG. 14A in a first position, in accordance with an aspect of the present invention.

Another spinal cage system 900 is shown in FIGS. 14A-14B. The spinal cage system 900 may include a cage 910, the external plate 130, and a rod 840 with a flange member 950. The external plate 130 may be of the type described above with reference to FIGS. 1A-1E, which will not be described again here for brevity sake. The cage 910 may be similar to the cage 810 and may include the body portion 112, at least one opening 114, the plurality of protrusions 116, the opening 118, and the first and second holes 120, 122 of the cage 810, as described in greater detail above with reference to FIGS. 13A-13E. As depicted, the cage 910 may also include, for example, a first slot 912 and a second slot 914. The slots 912, 914 may engage the opening 118 and extend from the anterior surface of the cage 910 through to the opening 114. The slots 912, 914 may be sized and shaped to receive the flange member 950.

The rod 840 may also include the flange member 950 near the second end 844 of the rod 840. The flange member 950 may be fixed to the rod 840 in a position perpendicular to the rod 840, as shown in FIGS. 14A-14B, or alternatively rotatably connected to the rod 840 as described in greater detail above. The flange member 950 may include a first flange 952 coupled to a first side of the rod 840 and a second flange 954 coupled to a second side of the rod 840. The first side may be opposite the second side of the rod. The first flange 952 may be positioned relatively perpendicular to the rod 840 in a first direction and the second flange 954 may be positioned relatively perpendicular to the rod 840 in a second direction. The first and second directions may be opposite each other such that the first and second flanges 952, 954 are parallel to each other at the points of attachment to the rod 840 and each flange 952, 954 extends in an opposite direction from the other flange 952, 954. The first and second flanges 952, 954 may be fixed directly to the rod 840 or attached to the rod with a connecting member, such as connecting member 856 described in greater detail above with reference to FIGS. 13A-13C.

The rod 840 may be sized to be received in opening 118 and the flanges 952, 954 may be sized to be received in the slots 912, 914, respectively. The opening 118 and slots 912, 914 allow the rod to slide in an anterior/posterior direction within the cage 910 both prior to and after insertion into a patient. The rod 840 may also be sized to either allow for rotation of the rod 840 within the opening 118 of the cage 910 or to fix the rod 840 from rotating within the opening 118 of the cage 910 once the flanges 952, 954 are positioned within the opening 114.

The spinal cage system 900 may also include at least one locking mechanism 160, as shown in FIG. 14B. The at least one locking mechanism 160 may be of the type described above with reference to spinal cage system 100. The at least one locking mechanism 160 may be used to assemble the spinal cage system 900. For example, the spinal cage system 900 may be assembled by obtaining a rod 840 with the flange member 950. Next, the end of the rod 840 with the flange member 950 may be inserted into the opening 118 and slots 912, 914 in the cage 910. The external plate 130 may be attached to the rod 840 prior to insertion of the flange member 950 into the cage 910 or alternatively after the flange member 950 is inserted into the cage 910. The external plate 130 may be attached to the rod 840 using at least one locking mechanism 160, as shown in FIG. 14B, and described in greater detail above with reference to FIGS. 13B-13D, which will not be described again here for brevity sake. Once the external plate 130 is secured to the rod 840 and the cage 910 is positioned between the patient's vertebral bodies, the surgeon may move the external plate 130 in an anterior-posterior direction until the desired alignment with the adjacent vertebral bodies is achieved. Then, the surgeon may rotate the external plate 130 which will in turn rotate the rod 840 and coupled flange member 950. The flanges 952, 954 of the flange member 950 will rotate and each engage at least one of the plurality of protrusions 116 on opposite side walls of the cage 910. In another embodiment, the plate 130 may be configured to rotate independent of the rod 840, to allow the surgeon to rotate the rod 840 to secure the flanges 952, 954 each in a protrusion 116 to maintain the desired anterior-posterior position, while also providing the surgeon additional flexibility for positioning the external plate 130 on the patient's vertebral bodies. Once the external plate 130 and cage 910 are in the desired position, fasteners (not shown), for example, bone screws, may be inserted into the first and second holes 120, 122 to secure the cage 910 to the patient's adjacent vertebral bodies. In addition, fasteners (not shown), such as bone screws, may be inserted through the holes 134 in the external plate 130 to secure the external plate 130 to the patient's vertebral bodies.

Optionally, a removable washer 216 could be inserted into the opening 118 of cages 810, 910 after insertion of the flange member 850, 950 to prevent the flange member 850, 950 from sliding out of the cage 810, 910 prior to coupling the flange member 850, 950 to the plurality of protrusions 116 of the cage 810, 910.

The spinal cage systems 100, 200, 300, 400, 500, 600, 700, 800, 900 may be used, for example but not limited to, in the cervical, lumbar, and/or thoracic regions of the spine. Further, the spinal cage systems 100, 200, 300, 400, 500, 600, 700, 800, 900 may allow for insertion by different approaches for different vectors of the spine. For example, it is contemplated that the spinal cage systems 100, 200, 300, 400, 500, 600, 700, 800, 900 may be inserted into a patient's lumbar region or thoracic region from lateral or anterior approaches. In addition, the spinal cage systems 100, 200, 300, 400, 500, 600, 700, 800, 900 may each have different shaped cages 110, 210 depending on the surgical procedure being performed and the optimal cage design desired by the surgeon.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

As may be recognized by those of ordinary skill in the art based on the teachings herein, numerous changes and modifications may be made to the above-described and other embodiments of the present invention without departing from the scope of the invention. The cage, external plate, rod, internal plate, locking mechanism, and other components of the device and/or system as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1A-1E, FIGS. 2A-2F, FIGS. 4A-4E, FIGS. 5A-5E, FIGS. 6A-6E, FIGS. 7A-7E, FIGS. 8A-8I, FIGS. 13A-13D, and FIGS. 14A-14B may all be used interchangeably and in alternative combinations as would be modified or altered by one of skill in the art. Additionally, as may be recognized by those or ordinary skill in the art based on the teachings herein, the locking mechanism can be of any of numerous types of locking mechanisms that are currently known or that later become known to secure or otherwise couple a plate or stop member to a rod; additionally, more than one locking mechanism could be employed. Accordingly, this detailed description of the currently-preferred embodiments is to be taken in an illustrative, as opposed to limiting of the invention.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed:
1. A spinal cage system, comprising:
   a cage with a body portion having a first end and a second end, comprising:
      at least one opening positioned between the first end and the second end;
      a center opening positioned relatively perpendicular to the at least one opening, wherein the center opening comprises:
         an interior surface; and
         a plurality of protrusions positioned circumferentially around the interior surface of the center opening;
   an external plate with a central hole and at least two holes positioned on opposite sides of the central hole; and
   a rod with a first end and a second end, wherein the rod extends through the center opening in the cage, the first end couples to the external plate, and the second end extends into the at least one opening;

wherein at least one of the plurality of protrusions engage a portion of the rod between the first end and the second end.

2. The spinal cage system of claim 1, further comprising:
at least one locking mechanism comprised of a first locking mechanism and a second locking mechanism.

3. The spinal cage system of claim 2, wherein the second locking mechanism secures the external plate to the first end of the rod; and
wherein the center opening includes an interior surface that is comprised of at least one of a smooth interior surface section and an interior section having a plurality of teeth disposed thereon.

4. The spinal cage system of claim 1, further comprising a first hole and a second hole, the first hole being angled in a first direction and the second hole being angled in a second direction.

5. The spinal cage system of claim 1, wherein the rod comprises:
a plurality of grooves extending from the first end to the second end and parallel to a longitudinal axis of the rod, and wherein the plurality of grooves engage the plurality of protrusions of the center opening.

6. The spinal cage system of claim 2, wherein the at least one locking mechanism comprises:
at least one top member; and
at least one bottom member configured to couple to the top member.

7. The spinal cage system of claim 1, further comprising:
an internal plate with at least one opening configured to engage the rod, wherein the first locking mechanism secures the internal plate to the rod at the second end.

8. The spinal cage system of claim 1, further comprising:
a flange member coupled to the second end of the rod.

9. The spinal cage system of claim 8, wherein the flange member comprises:
a first flange fixed to a first side of the rod; and
a second flange fixed to a second side of the rod.

10. The spinal cage system of claim 1, wherein the cage further comprises:
a first slot extending in a first direction from the center opening and into the at least one opening; and
a second slot extending in a second direction from the center opening and into the at least one opening; wherein the first slot is configured to allow a first flange to pass there through and the second slot is configured to allow a second flange to pass there through.

11. The spinal cage system of claim 1, wherein the least one opening further comprises at least two surfaces having a plurality of protrusions extending therefrom, wherein when the rod is inserted and rotated, a first flange engages at least one protrusion and a second flange engages a second protrusion to secure the rod in a fixed position.

12. A cage system, comprising:
a cage, wherein the cage comprises:
a body portion;
at least one opening through the body portion in a superior-inferior direction;
at least one hole in an anterior surface of the body portion extending into the at least one opening;
a center opening in the anterior surface of the body portion, wherein the center opening is positioned adjacent to at least one of the at least one hole, and wherein the center opening is positioned relatively perpendicular to the at least one opening; and
a plurality of protrusions on at least one interior surface of the at least one opening of the cage extending between a first end and a second end of the cage; and
at least one locking screw assembly, wherein the at least one locking screw assembly comprises:
at least one locking member sized to be received in the at least one hole of the cage;
at least one fastener configured to pass through the at least one hole in the cage and engage the at least one locking member, wherein the at least fastener has a head portion with an opening extending through the head portion and a plurality of grooves positioned around an exterior surface of the head portion; and
a shaft portion extending out from the head portion and having a plurality of threads on at least a portion of an exterior surface of the shaft portion.

13. The cage system of claim 12, wherein the at least one hole comprises:
at least one first hole angled in a first direction; and
at least one second hole angled in a second direction.

14. The cage system of claim 13, wherein the at least one hole comprises:
a first section; and
a second section adjacent to the first section and extending into the at least one opening in the body portion, wherein the first section and second section are threaded.

15. The cage system of claim 14, wherein the first section has a larger diameter than the second section.

16. The cage system of claim 12, wherein the at least one locking member comprises:
a body with an exterior surface;
an opening extending from a top to a bottom of the body defining an interior surface;
a smooth portion on the interior surface near a first end;
a grooved portion on the interior surface adjacent to the smooth portion; and
at least one thread on the exterior surface.

17. The cage system of claim 12, wherein the plurality of grooves on the head portion of the fastener are configured to engage the grooved portion of the locking member to secure the at least one locking screw assembly in the at least one hole of the cage.

* * * * *